United States Patent
Kaji et al.

(10) Patent No.: US 8,508,219 B2
(45) Date of Patent: Aug. 13, 2013

(54) OBJECT STATE DETECTION APPARATUS AND METHOD

(75) Inventors: Ryosaku Kaji, Tsukuba (JP); Mitsuaki Shimizu, Tsukuba (JP); Kiyomi Hirota, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 1142 days.

(21) Appl. No.: 12/431,300

(22) Filed: Apr. 28, 2009

(65) Prior Publication Data

US 2010/0019759 A1    Jan. 28, 2010

(30) Foreign Application Priority Data

Apr. 30, 2008  (JP) ................................. 2008-119270
Apr. 28, 2009  (JP) ................................. 2009-109983

(51) Int. Cl.
*G01B 7/14*    (2006.01)

(52) U.S. Cl.
USPC ............. 324/207.22; 324/207.26; 324/207.11

(58) Field of Classification Search
USPC ......................................................... 324/144
See application file for complete search history.

(56) References Cited

U.S. PATENT DOCUMENTS

| | | | |
|---|---|---|---|
| 6,781,380 B1 * | 8/2004 | Wiegert | 324/329 |
| 6,796,799 B1 | 9/2004 | Yoshiike et al. | |
| 7,242,306 B2 * | 7/2007 | Wildman et al. | 340/573.1 |
| 7,584,048 B2 * | 9/2009 | Pham et al. | 701/434 |
| 7,603,894 B2 * | 10/2009 | Breed | 73/146 |
| 7,948,430 B2 * | 5/2011 | Konishi et al. | 342/27 |
| 8,068,051 B1 * | 11/2011 | Osterweil | 342/28 |
| 2004/0257267 A1 | 12/2004 | Mafune et al. | |
| 2007/0103328 A1 * | 5/2007 | Lakshmanan et al. | 340/686.6 |
| 2007/0132582 A1 | 6/2007 | Kaji et al. | |
| 2007/0150381 A1 * | 6/2007 | Pippia et al. | 705/28 |
| 2008/0185540 A1 * | 8/2008 | Turner et al. | 250/515.1 |
| 2008/0292087 A1 * | 11/2008 | Agrawal et al. | 379/211.02 |
| 2008/0309344 A1 * | 12/2008 | Larsen | 324/326 |
| 2008/0309491 A1 * | 12/2008 | Gillard et al. | 340/572.1 |
| 2008/0318684 A1 * | 12/2008 | Rofougaran | 463/39 |
| 2009/0267823 A1 | 10/2009 | Konishi et al. | |
| 2009/0284350 A1 * | 11/2009 | Konishi et al. | 340/10.1 |

FOREIGN PATENT DOCUMENTS

| | | |
|---|---|---|
| EP | 0903707 A2 | 3/1999 |
| JP | 2004-226089 A | 6/1999 |
| JP | 2001-74855 | 3/2001 |
| JP | 2003-185735 | 7/2003 |
| JP | 11-151209 A | 8/2004 |
| JP | 2007-163249 | 6/2007 |
| WO | WO 2007/058302 A1 | 5/2007 |

* cited by examiner

*Primary Examiner* — Richard Isla Rodas

(74) *Attorney, Agent, or Firm* — Wolf, Greenfield & Sacks, P.C.

(57) ABSTRACT

There is provided an apparatus and method for identifying and measuring the electric field strength which occurs from each of RFID tags arranged in a detection target space by a receiver to grasp the state of an object. The apparatus is provided with m (m>=1) electromagnetic field generation means provided near a space, the space being occupied by the object when the object is in a particular state; n (n>=1) electric field strength measurement means for identifying and measuring electric field strength which occurs from each of the m electromagnetic field generation means; characteristic extraction means for calculating characteristics from m×n time-series data of the electric field strength; and state identification means for identifying, by statistical processing, a state from the characteristics and characteristic data in each state for learning.

14 Claims, 29 Drawing Sheets

OBJECT STATE DETECTION APPARATUS AND METHOD

BACKGROUND OF THE INVENTION

1. Field of the Invention

The present invention relates to an apparatus and a method for measuring and identifying the electric field strength generated from each of transmitters arranged in a detection target space by a receiver to grasp a state of an object such as a person or a thing.

2. Description of the Related Art

RFID (the abbreviation of Radio Frequency IDentification) refers to what is for exchanging information with a tag in which ID information is embedded, via short-distance wireless communication using an electromagnetic field, a radio wave or the like, and also refers to the whole technology therefor.

Especially in Japan, the movement of attempting to apply the RFID technology to the fields of welfare and crime prevention has gathered momentum with the advent of the aged society. For example, it is under examination to realize, in a hospital, information support so that a medical staff can efficiently work by attaching RFID tags to the medical staff, patients, medical equipment and medical products, collecting location information about persons and things by antennas arranged at various places via a network such as a LAN, and performing centralized control of the location information by a server, and to utilize the RFID tags for location management of prisoners in a prison.

It is also conceivable to realize higher quality services by mounting various sensors on RFID tags, attaching the RFID tags to persons, detecting a particular state and an abnormal state of the person or things, transmitting information about the state and processing collected information.

However, in the fields of welfare and crime prevention, places to be monitored are often private spaces of people who are to receive services, and they hate to attach a device in such spaces. They may forget to attach the device. Even if devices are attached to prisoners in a prison, a prisoner who does not want to be known of his state may pretend to attach the device. Detailed examples will be described below.

Statistically, a bathroom, a restroom and a dressing/undressing space account for a high percentage among places where elderly people fall down because of a brain or heart attack. There exists medical technology in which earlier discovery enables more appropriate treatment to significantly reduce aftereffects. It is necessary, in such particular closed spaces where only an elderly person exists and early discovery by a third person is difficult, to detect a state in which the elderly person has fallen down and cannot move and inform it to a person in charge of nursing care as soon as possible.

As described in Japanese Patent Laid-Open No. 11-151209, in a nursing care home, a nurse goes around checking patient rooms and beds because it is necessary to grasp whether patients are in beds provided in the patient rooms, that is, whether the patients are sleeping in the beds or wandering away from the beds in order to grasp the patients' absence-from-bed/presence-in-bed states. However, it is impossible to continuously go around checking all the patients' beds. Thus, it is necessary to detect a state in which an elderly person does not exist in a particular space, i.e., on a bed, and inform it to a person in charge of nursing care of the elderly person as soon as possible.

From the viewpoint of crime prevention, bad deeds taking advantage of cognitive impairment of elderly persons are increasing, such as violence and robbery of money and valuables in nursing care homes. In order to cope with this, it is necessary to record an abnormal movement around a bed and take a picture of persons who exist at that time. However, since an elderly person or his or her guardian hates a camera being placed in the room, it is necessary to install the camera outside the room. That is, it is necessary to take a picture of a person who comes out of the room immediately after it is detected that the movement of the elderly person is abnormal in the particular space, i.e., around the bed, to record and identify the suspicious person.

In business companies, acts of information collectors infiltrating inside offices, such as industrial spies, are a problem. An event was reported and much talked about that data was stolen from a computer to leak technical information to a foreign company. Such a primitive method has been repeated again and again to steal information. In order to prevent this, it is proposed to have employees carry RFID tags, install an antenna in an individual employee's booth and take a picture when an employee having a different ID intrudes into a booth. However, an employee with a malicious intention does not do such a malicious act with his own ID attached to him. That is, it is necessary to detect and record existence of a third person other than the person in charge of the booth, even if the third person does not have any ID.

As described above, in the fields of welfare and crime prevention, it is much more often appropriate to install a sensor-attached RFID tag in a space where a problem may occur to collect information rather than attaching a sensor or an RFID tag to a detection target. Since it is often the case that positions where a problem may occur are distributed in multiple places, it is desirable to reduce the cost by adapting the sensor be able to monitor a wide range of space, or assigning one sensor to each of the multiple places and minimizing the function of the sensor itself.

A network camera is a sensor having a function of detecting a state of a person or a thing and transmitting information not by being attached to a human body but by being provided in an environment. The network camera makes it possible to obtain information from which a state of a person lying down, a state of receiving violence, or the like can be judged. However, a great amount of information is used to detect a simple state, and there is a disadvantage that the information transmission cost and the information processing cost are high. Furthermore, consideration must be given to a privacy problem to install a camera in a private space.

A current-collection-type infrared sensor can contactlessly collect states of a person or a thing similarly to a camera while securing privacy, and the amount of information is not large, and the information processing cost is low. However, it is known to be easily affected by steam, dust or stain and excessively issue a wrong signal.

A Doppler radar used for an activation switch of an automatic door and the like does not malfunction due to steam, dust or stain, and its function is sufficient to detect existence. However, its installation is large-scale. In Japanese Patent Laid-Open No. 2004-226089, a lock control apparatus is proposed as a Doppler-radar-type sensor for which the large-scale installation and cost problems have been overcome. However, since the Doppler-radar-type sensor is a radar capable of observing not only the position but also the moving speed of an observation target by observing variation in frequency due to the Doppler effect, it has functions unnecessary for detecting a still state as described above, and the cost per sensor is higher for the functions.

SUMMARY OF THE INVENTION

In order to detect that a person or a thing is in a particular state without using a camera and without malfunction due to dust or stain, it is desirable to arrange radio-wave-sensor-mounted-type REFIDs to act as a tentacle in a target space. In order to suppress the cost per sensor, it is necessary to draw a sensor function by utilizing change in the strength of the radio wave itself having ID information about the RFID tag thereon, without equipping the Doppler radar function. Thus, it is an object of the present invention to provide an apparatus and method for identifying and measuring the electric field strength which occurs from each of RFID tags arranged in a detection target space by a receiver to grasp the state of an object.

To solve the above problem, the present invention first provides an apparatus for detecting a state of an object, comprising:

m (m>=1) electromagnetic field generation means provided near a space, the space being occupied by the object when the object is in a particular state;

n (n>=1) electric field strength measurement means for identifying and measuring electric field strength generated from each of the m electromagnetic field generation means;

characteristic extraction means for calculating characteristics from m×n time-series data of the electric field strength; and state identification means for identifying, by statistical processing, the state from the characteristics and characteristic data in each state for learning.

Second, the present invention provides the object state detection apparatus, wherein each of the electromagnetic field generation means has an antenna structure for controlling spatial distribution of accumulated fields.

Third, the present invention provides the object state detection apparatus, wherein the efficiency of radiation of an electromagnetic field into free space by the electromagnetic field generation means changes when the object exists nearby.

Fourth, the present invention provides the object state detection apparatus, wherein the n electric field strength measurement means are arranged so that the states of electromagnetic fields which occur from the electromagnetic field generation means changing due to existence of the object can be measured separately from one another.

Fifth, the present invention provides the object state detection apparatus, wherein the characteristic extraction means converts m×n electric field strength values at the time when the space is in a still state into vector data with m×n elements.

Sixth, the present invention provides the object state detection apparatus, wherein the state identification means learns a upper-limit value and the lower-limit value of the electric field strength, for each of the m×n data, from characteristic data of each still state which has been collected for learning, and identifies a state by the fact that input character data is between the upper-limit value and the lower-limit value of the electric field strength.

Seventh, the present invention provides the object state detection apparatus, wherein the object state detection apparatus executes alarm processing in accordance with the state identification by the state identification means.

Eighth, the present invention provides the object state detection apparatus, wherein the object state detection apparatus performs processing of photographing data of the space in accordance with the state identification by the state identification means.

Ninth, to solve the above problem, the present invention further provides a method for detecting a state of an object, comprising:

providing m (m>=1) transmitters near a space, the space being occupied by the object when the object is in a particular state;

identifying and measuring electric field strength which occurs from each of the m transmitters by n (n>=1) receivers;

calculating characteristics from m×n time-series data of the electric field strength; and identifying, by statistical processing, a state from the characteristics and characteristic data in each state for learning.

Tenth, the present invention provides the object state detection method, wherein each of the transmitters has an antenna structure for controlling spatial distribution of accumulated fields.

Eleventh, the present invention provides the object state detection method, wherein an efficiency of radiation of an electromagnetic field into free space by each of the transmitters changes when the object exists nearby.

Twelfth, the present invention provides the object state detection method, wherein the n receivers are arranged so that the states of electromagnetic fields which occur from the transmitters changing due to existence of the object can be measured separately from one another.

Thirteenth, the present invention provides the object state detection method, wherein the characteristic calculation processing converts m×n electric field strength values at the time when the space is in a still state into vector data with m×n elements.

Fourteenth, the present invention provides the object state detection method, wherein the state identification processing learns a upper-limit value and a lower-limit value of the electric field strength, for each of the m×n data, from characteristic data of each still state which has been collected for learning, and identifies the state by the fact that input character data is between the upper-limit value and the lower-limit value of the electric field strength.

Fifteenth, the present invention provides the object state detection method wherein alarm processing is executed in accordance with the state identification.

Sixteenth, the present invention provides the object state detection method wherein processing of photographing data of the space is performed in accordance with the state identification.

According to the present invention, by using only an RFID tag provided in an environment without having a person carry a sensor, it is possible to detect that a person is in a particular state near the tag.

According to the present invention, by installing an RFID tag near the floor especially in a toilet or a restroom, it is possible to detect a state in which a person lies down on the floor.

According to the present invention, by installing an REFID tag on a desk in a personal booth in an office, and having the owner of the desk carry an another RFID tag, it is possible that nothing happens when the owner's ID is detected, and photographing, alarm, reporting or the like is triggered when the owner's ID is not detected (the owner is absent) and the electric field strength of the RFID provided on the desk shows an abnormal value.

According to the present invention, by attaching an RFID tag on the back of the bed, it is possible to judge an absence-from-bed state or a presence-in-bed state. It is also possible to record whether or not there is any abnormality in the movement of an elderly person in bed and, for example, expose a possibility of the elderly person receiving violence. In this case, it is also possible to take a picture with the consent of the subject in question or his or her guardian to leave evidence.

According to the present invention, it is possible to contactlessly monitor stillness and movement of liquid in a container and inform an abnormal state.

According to the present invention, it is possible to contactlessly monitor an electric noise of such as an electric wire and record and inform an abnormal performance of an electrical product.

BRIEF DESCRIPTION OF THE DRAWINGS

FIG. 19 shows the outline of an installation situation when an object state detection apparatus and method according to a fifth embodiment of the present invention is applied to monitoring of abnormalities of an electrical system and measurement apparatuses and the like;

DETAILED DESCRIPTION OF THE PREFERRED EMBODIMENTS

Embodiments of the present invention will be described below with reference to drawings.

First Embodiment

An object state detection apparatus and method according to a first embodiment of the present invention will be described with reference to drawings.

Figure 1:
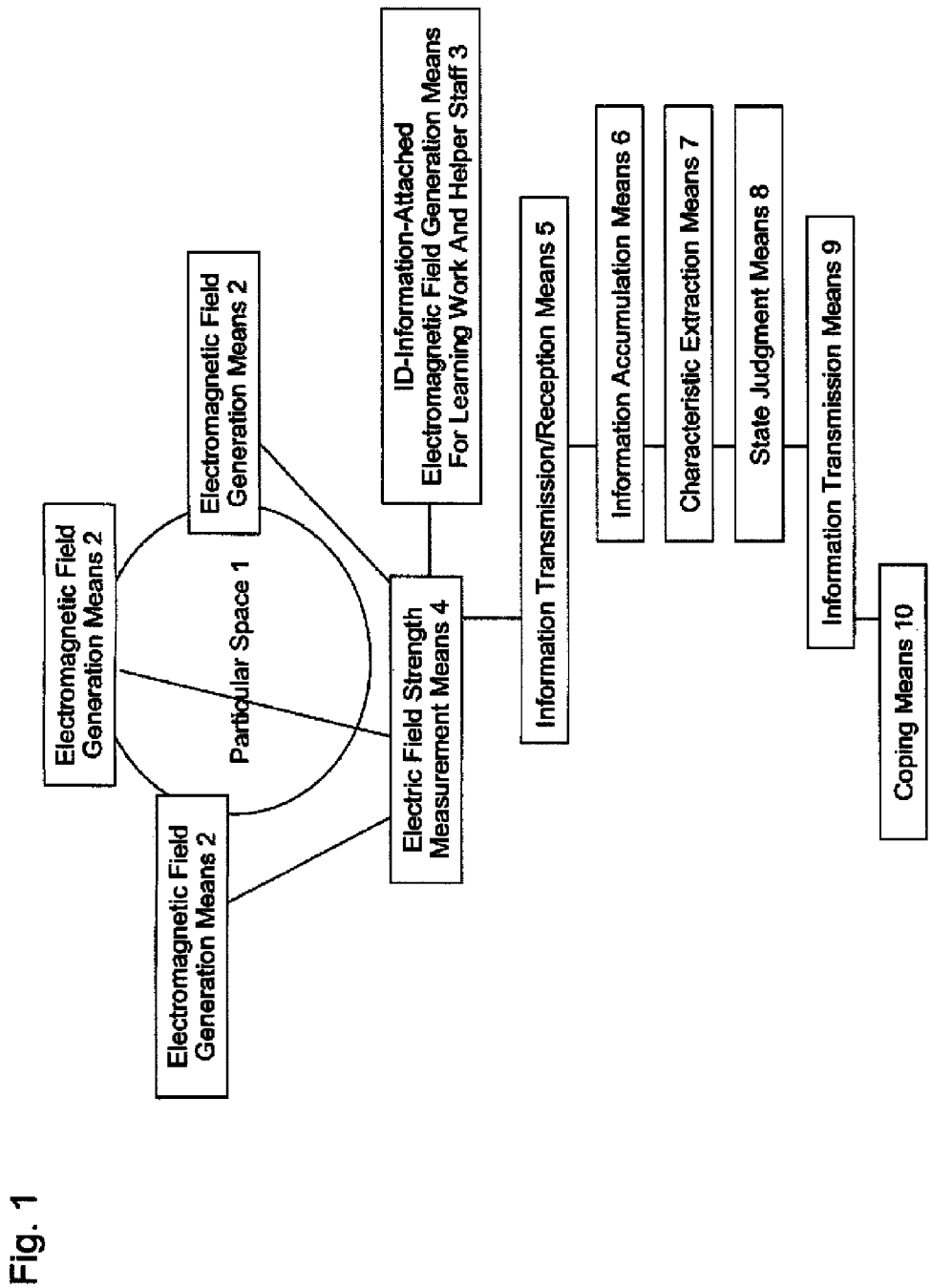
FIG. 1 is a schematic diagram of an apparatus and method for detecting a particular state of an object according to the present invention.

FIG. 1 is a schematic diagram of the apparatus and method for detecting a particular state of an object which utilize the fact that the state of an object can be identified by the object occupying a large part of a particular space, in the first embodiment of the present invention. At least one ID-information-attached electromagnetic field generation means 2 is provided near a particular space 1. At least one electric field strength measurement means 4 for identifying and measuring, for each ID, the electric field strength of the ID-information-attached electromagnetic field generation means 2 is provided. The electric field strength measurement means 4 is connected to information accumulation means 6 via information transmission/receiving means 5. The information accumulation means 6 comprises characteristic extraction means 7 and state judgment means 8. The state judgment means 8 is connected to coping means 10 via information transmission means 9. Characteristic information used by the characteristic extraction means 7 may be separately given in advance, or it is also possible to cause the characteristic extraction means 7 to automatically learn the characteristic information. For this purpose, ID-information-attached electromagnetic field generation means 3 for automatic learning is newly prepared so that the characteristic extraction means 7 automatically and additionally learns the characteristic information only while the electric field strength measurement means 4 acquires this ID information.

For example, when a person falls down in a restroom and cannot move, the electric field strength measurement means 4 detects the ID of an electromagnetic field generated from electromagnetic field generation means 2 provided near the floor, one of ID-information-attached electromagnetic field generation means 2; the characteristic extraction means 7 works upon ID-attached electric field strength information collected into the information accumulation means 6; and the state judgment means 8 detects a fallen state and transmits a signal to the coping means 10.

Figure 2:
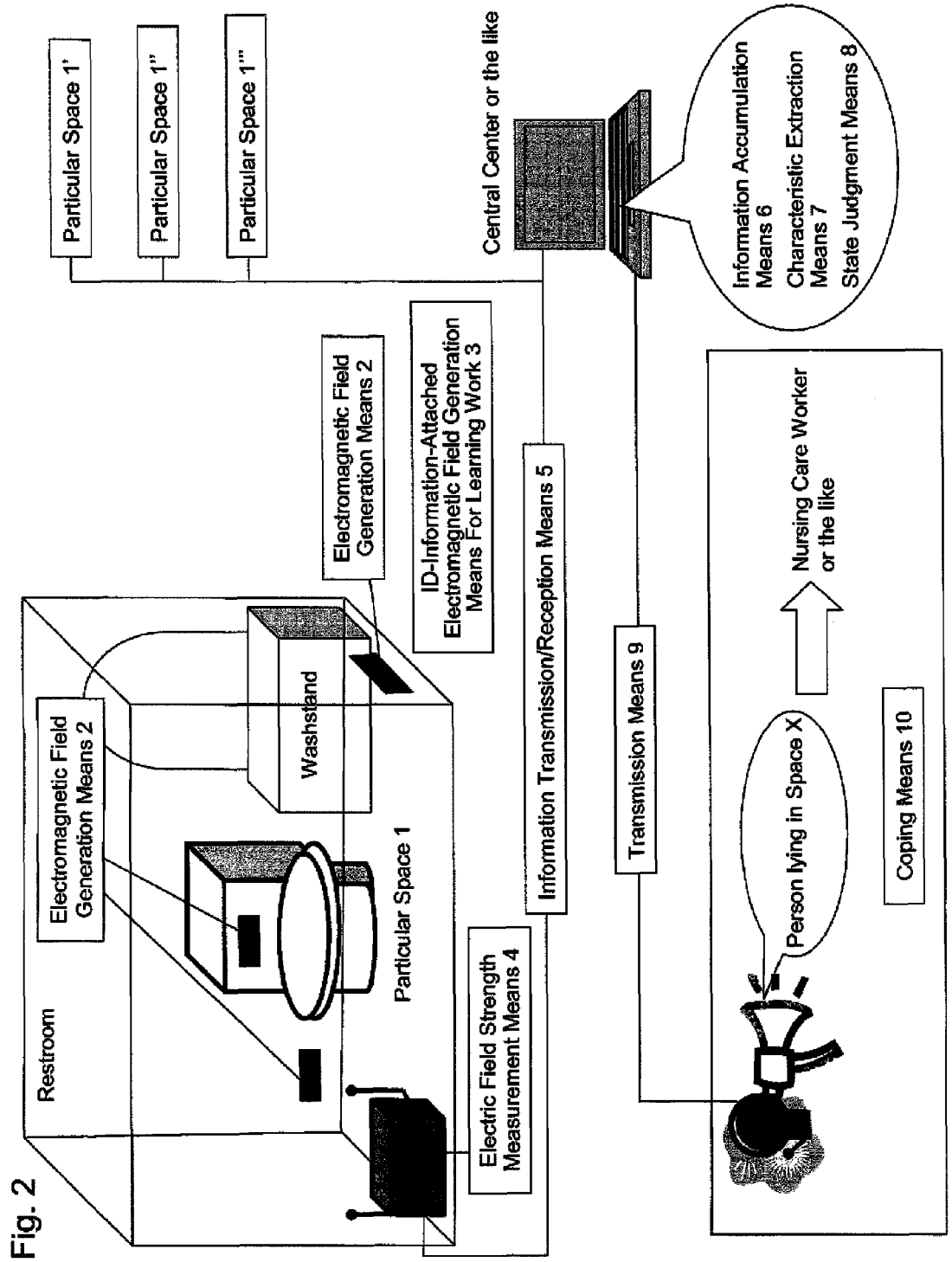
FIG. 2 shows the outline of installation situation when the apparatus and method for detecting a state of an object according to a first embodiment of the present invention is applied to detection of a fallen person.

FIG. 2 is a diagram showing a detailed installation state and shows a restroom where a toilet bowl and a washstand are arranged as an example. At least one ID-information-attached electromagnetic field generation means 2 is provided near a space expected to be occupied by a person in a fallen state. The electric field strength measurement means 4 is provided within a range where the electric field strength of the electromagnetic field generation means 2 can be measured and advantageously provided so that the space to be detected is located between the electromagnetic field generation means 2 and the electric field strength measurement means 4. The information accumulation means 6, the characteristic extraction means 7, the state judgment means 8, the transmission means 9 and the coping means 10 are not necessarily required to be provided near the particular space 1. They may be provided in a distant space such as in a nurse center, in a control panel room and on an information manager's desk.

Figure 3:
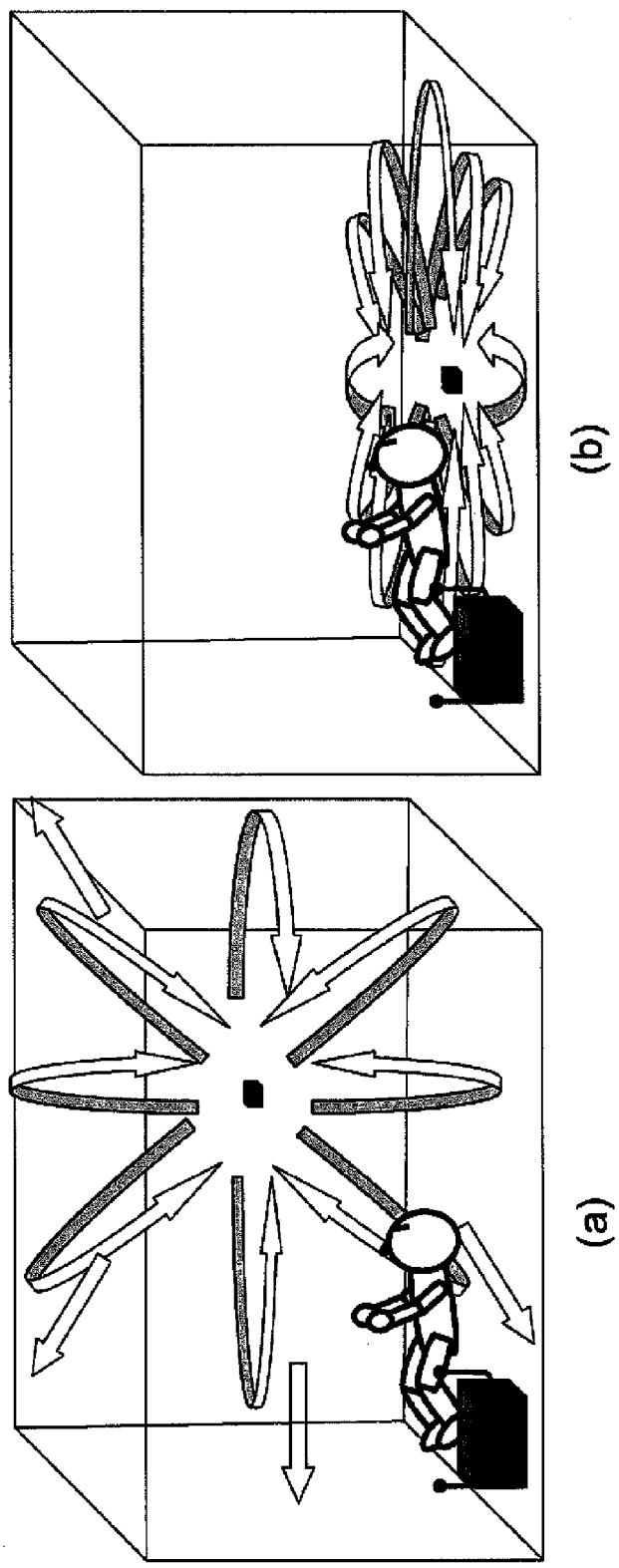
FIG. 3 is a diagram for illustrating the antenna structure of a tag.

In this case, the ID-information-attached electromagnetic field generation means 2 is an active-type RFID tag, and it is desirable to design and devise it so that the electromagnetic field emission efficiency drastically changes when a person or a thing is in a particular state near it. For this purpose, it is necessary to adopt an antenna structure for controlling the distribution state of near fields referred to as accumulated fields, without completely performing impedance matching with free space, so that the emission efficiency of an electromagnetic field drastically changes due to influence of an object near the tag as illustrated in FIG. 3(B), rather than adopting the antenna structure for performing impedance matching with free space for efficiently emitting an electromagnetic field into the free space, which is a guiding principle for designing an ordinary active-type tag, as illustrated in FIG. 3(A). The electric field strength measurement means 4 is a tag reader. It is connected to the information accumulation means 6 via a serial cable, which is the information transmission/receiving means 5, a wired/wireless LAN or PLC, or the like, and it transmits information about the electric field strength of a measured ID in response to a request by the information accumulation means 6.

As the coping means 10, photographing of evidence by a camera, continuous or intermittent activation of an alarm by a lamp or a voice, and display of an alarm on a computer monitor are conceivable, but the detailed method is not especially limited. In the case of displaying an alarm on a computer monitor, all of the information transmitting/receiving means 5, the characteristic extraction means 7, the state judgment means 8, the transmission means 9 and the coping means 10 may be included in the same computer.

Figure 4A:
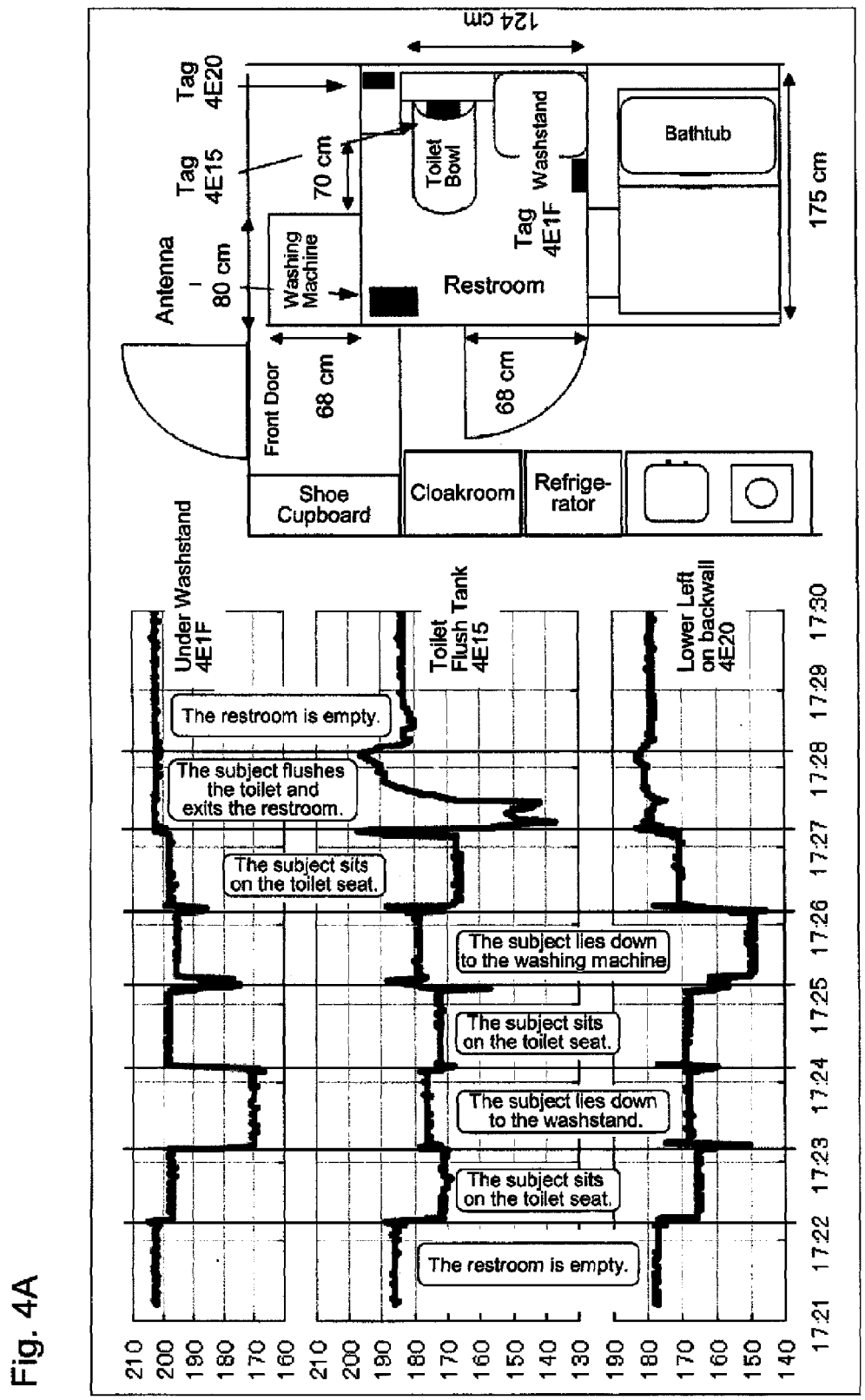
FIG. 4A is a diagram showing an example of fluctuation of the electric field strength value according to the first embodiment of the present invention together with information about a person's acts in a restroom, and detailed installation situation of the tag and the antenna.
Figure 4B:
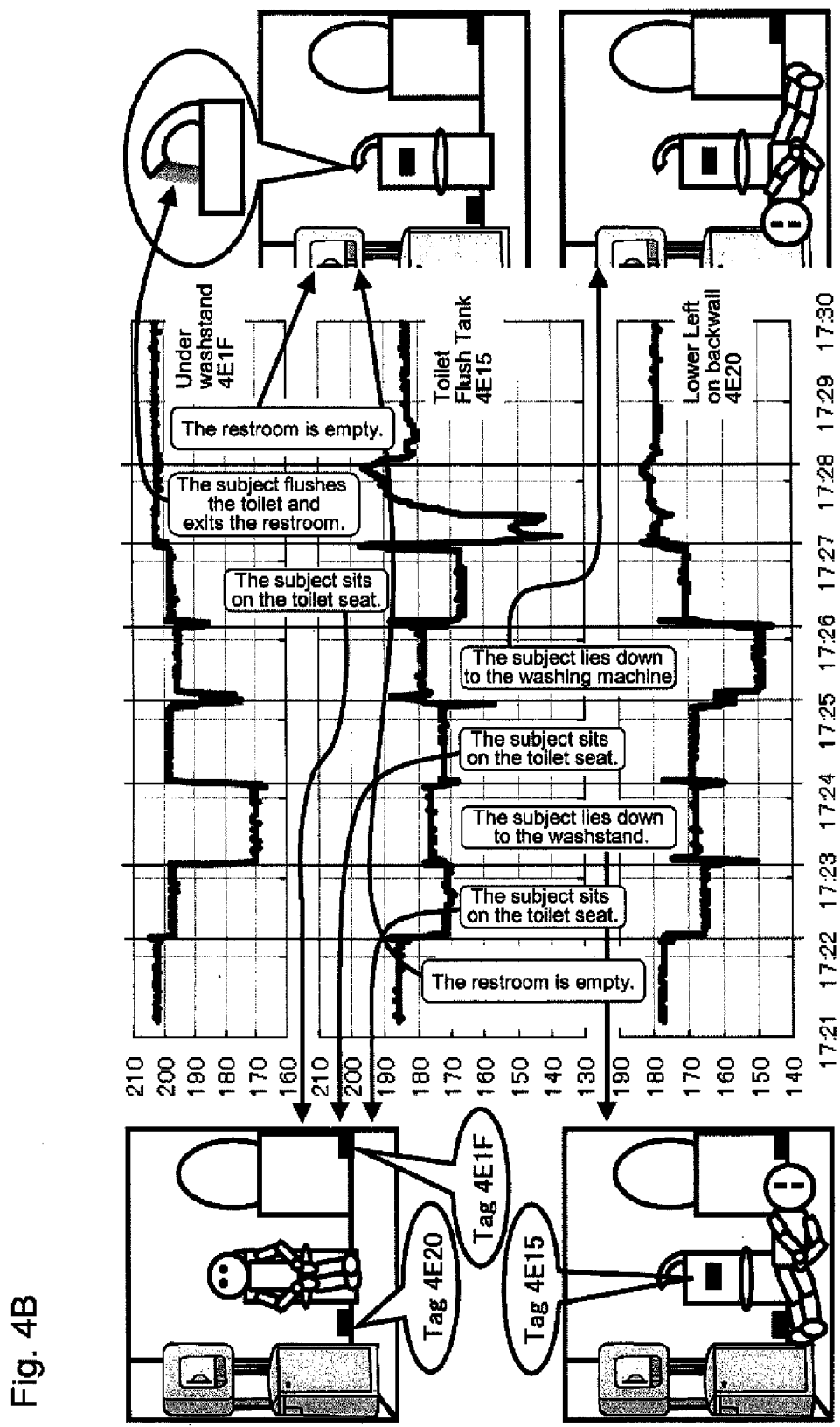
FIG. 4B is a diagram showing an example of fluctuation of the electric field strength value according to the first embodiment of the present invention together with information about a person's acts in a restroom, and detailed installation situation of the tag and the antenna.

FIGS. 4A and 4B show an example of fluctuation of an electric field strength value outputted by the electric field strength measurement means 4 together with information about person's actions in a restroom. An accurate arrangement of tags, electromagnetic field generation means and electric field strength measurement means is also shown on the right side of FIG. 4A. As seen from the diagrams, when there is not a person in the restroom and water is not moving, the value of the electric field strength is almost constant. Even if there is a person in the restroom, the electric field strength is almost constant if he is in a still state. While water in the toilet bowl is flowing, a tag 4E15 provided on the flush tank in the restroom shows great fluctuation of the electric field strength, but the other tag 4E1F, which is provided on the wall under the washstand and near the floor (see FIG. 2 also), and tag 4E20, which is provided at the lower left position on the wall opposite to the entrance of the restroom and near the floor (see FIG. 2 also), do not show a large change. When the person falls on the washstand side, the electric field strength of the tag 4E1F provided under the washstand deviates downward in comparison with the other states. When the person falls on the washing machine side, the electric field strength of the tag 4E20 provided at the lower left on the wall opposite to the entrance of the restroom deviates significantly downward in comparison with the other states. These facts show that, by a person or water existing near a tag, the electromagnetic field formed by the tag is changed to a degree that an antenna can sufficiently identify.

Therefore, for example, as for the tag 4E1F provided under the washstand, by setting the range of the electric field strength in a normal state as 180 and above, and setting the fluctuation of the electric field strength in a still state to be 5 or below, it is possible to accurately judge that the person falls near under the washstand and cannot move when the electric field is departed from the range of the normal state and the fluctuation is, for example, 5 or below. As for the tag 4E20 provided on the left on the wall opposite to the entrance of the restroom, by setting the range of the electric field strength in a normal state as 160 and above, and setting the fluctuation of the electric field strength in a still state to be 5 or below, it is possible to accurately judge that the person falls on the left side of the restroom and cannot move when the electric field strength is departed from the range of normal state and the fluctuation is, for example, 5 or below. Of course, these thresholds are only an example in the case of FIGS. 4A and 4B, and it is desirable that they are set to suitable values appropriately.

Figure 5:
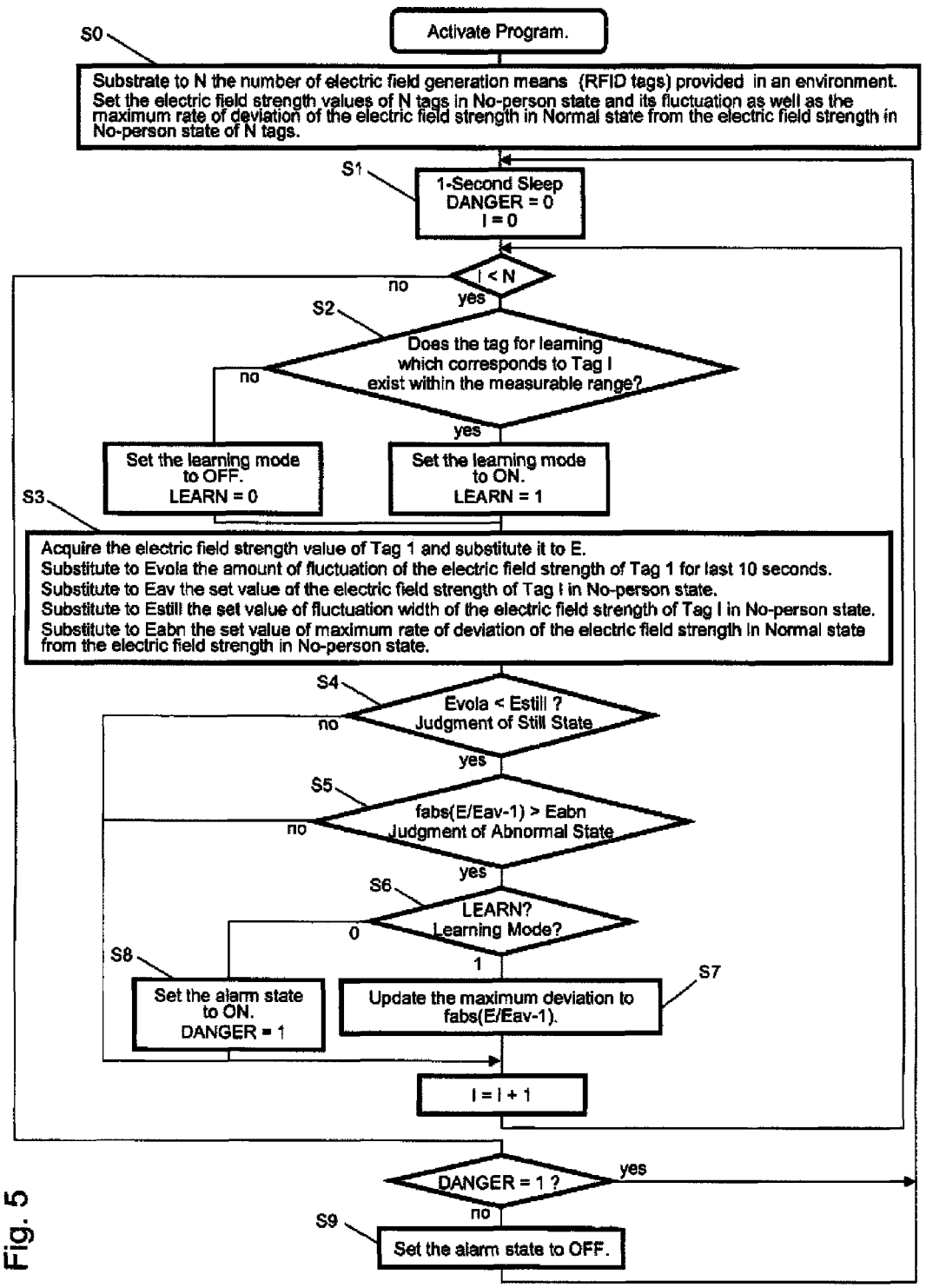
FIG. 5 is a flow diagram showing the operation of the object state detection apparatus and method according to the first embodiment of the present invention.

FIG. 5 shows an example of a basic operation of a fallen person detection system.

0: The electromagnetic field generation means 2 (RFID tag) provided near the particular space 1 periodically (for example once per second) generates specific ID information as a modulated electromagnetic wave using ASK or FSK, and the electric field strength measurement means 4 continues to identify and measure the electromagnetic wave for each ID.

1: In a computer or the like which comprises the information accumulation means 6, N, the number of RFID tags arranged in a space to be monitored, is set, and the initial values of the electric field strength in a no-person state and its fluctuation, and the maximum rate of deviation of the electric field strength in a normal state from the electric field strength in the no-person state of the N tags are set (step S0).

2: After 1-second sleep, an abnormal state detection flag is set to be off (DANGER=0), and a number 0 corresponding to the first tag number, among the RFID tags registered at step S0, is set for a variable I (step S1).

3: The computer which comprises the information accumulation means 6 checks whether the electric field strength of an RFID tag for leaning, which is corresponding to the electromagnetic field generation means 3 prepared for learning by the tag I, could be measured by the electric field strength measurement means 4 (step S2), and sets a learning mode to be on (LEARN=1) if the electric field strength could be measured. If the electric field strength of the tag for learning has not been measured, the learning mode is set to off (LEARN=0).

4: The information accumulation means 6 acquires the electric field strength value of the tag I from the electric field strength measurement means 4, calculates the amount of fluctuation of the electric field strength value for a predetermined period (10 seconds here), and reads the initial values of the electric field strength in the no-person state and its fluctuation width, and the maximum rate of deviation of the electric field strength in the normal state (a state in which a person exists but an abnormal state has not occurred) which have been set at step S0, from the electric field strength in the no-person state (step S3).

5: Judgment of a still state is performed (step S4). Specifically, if the amount of fluctuation of the electric field strength value for 10 seconds is smaller than the width set in advance, the characteristic extraction means 7 judges the still state (step S4).

6: If the still state is not judged to exist, the next tag number is substituted for the variable I, and the flow returns to step S2.

7: If the still state is judged to exist, judgment of an abnormal state is performed (step S5). Specifically, by the state judgment means 8, the rate of deviation from the electric field strength value in the no-person state which has been learned in advance is calculated; the deviation rate is compared with the maximum rate of deviation of the electric field strength in the normal state from the electric field strength in the no-person state which has been learned in advance; and the abnormal state is judged to exist if the deviation rate exceeds the maximum deviation rate (step S5).

8: If the abnormal state is not judged to exist, the next tag number is substituted for the variable I, and the flow returns to step S2.

9: If the abnormal state is judged to exist, it is judged whether the mode is the learning mode or not (step S6).

10: If the mode is the learning mode (LEARN==1), the initial value of the maximum deviation rate is updated to the current value (step S7); the next tag number is substituted for the variable I; and the flow returns to step S2. If the mode is not the learning mode (LEARN==0), an alarm state is set to be on, and an alarm flag is set up (step S8). Then, the next tag number is substituted for the variable I, and the flow returns to step S2. The alarm state may be any state for informing a dangerous state, such as a state of turning on and off each passage light, a state of turning on and off each light in an management center and a state of generating an alarm (step S8).

11: The above procedures 3 to 10 are performed for all the environment tags registered at step S0. If the alarm flag is not on (DANGER==1), it is interpreted that a dangerous state has ended, and the alarm is set to be off (step S9).

12: The procedure 2 is started again. Thereby, information about the N tags is acquired once per second.

The above function can be performed by a computer for a centralized control system. It is also possible that a microcomputer is included in the circuit of the electric field strength measurement means 4, so that it is possible to automatically detect the existence of a fallen person with high accuracy and issue an alarm.

Next, detailed methods for the characteristic extraction means 7 and the state judgment means 8 described above will be described.

For example, when an RFID tag is provided near the floor in the restroom to continuously measure its electric field strength as shown in FIG. 2, the width between the upper-limit value and the lower-limit value of the electric field strength within a predetermined period (for example, 10 seconds) is equal to or smaller than a small value S (for example, 4). That is, an electric field strength E is indicated by the following equations:

$$E\_low \text{ (no person)} < E < E\_high \text{ (no person)} \quad \text{(Equation 1)}$$

$$E\_high \text{ (no person)} - E\_low \text{ (no person)} <= S \quad \text{(Equation 2)}$$

When a person exists in the restroom and he is moving, the width between the upper-limit value and the lower-limit value of the electric field strength for a predetermined period (for example, 10 seconds) is larger than S (for example, 4). That is, the electric field strength E is indicated by the following equations:

$$E\_low \text{ (person existing and moving)} < E < E\_high \text{ (person existing and moving)} \quad \text{(Equation 3)}$$

$$E\_high \text{ (person existing and moving)} - E\_low \text{ (person existing and moving)} > S \quad \text{(Equation 4)}$$

When a person exists in the restroom and he stops moving, the width between the upper-limit value and the lower-limit value of the electric field strength for a predetermined period (for example, 10 seconds) is equal to or smaller than S (for example, 4). That is, the electric field strength E is indicated by the following equations:

$$E\_low \text{ (person existing and not moving)} < E < E\_high \text{ (person existing and not moving)} \quad \text{(Equation 5)}$$

$$E\_high \text{ (person existing and not moving)} - E\_low \text{ (person existing and not moving)} < S \quad \text{(Equation 6)}$$

As seen from Equations 1, 2, 5 and 6, when the width between the upper-limit value and the lower-limit value of the electric field strength for a predetermined period (for example, 10 seconds) is equal to or smaller than S (for example, 4), it can be judged that the person is not moving. Thus, the still state can be extracted.

The deviation rate is defined by the following equation, where the electric field strength in the still state of Equation 5 is denoted by E, and an average value Eav of the electric field strength in the no-person state of Equation 1 is used as a base.

$$Edev=|E/Eav-1|  \quad \text{(Equation 7)}$$

When a person is in a state of no movement at a position away from the tag on the floor (for example, a state of sitting on the toilet seat or a state of brushing his teeth before the washstand), the deviation rate of Equation 7 tends to be small. In comparison, when the person is in a state of no movement near the tag on the floor (that is, a state in which he lies down on the floor and cannot move), the deviation rate of Equation 7 becomes large. By designing and arranging the tags and the antenna appropriately so that the deviation rate difference is large, it is possible to judge the normal state and a dangerous state.

Figure 6:
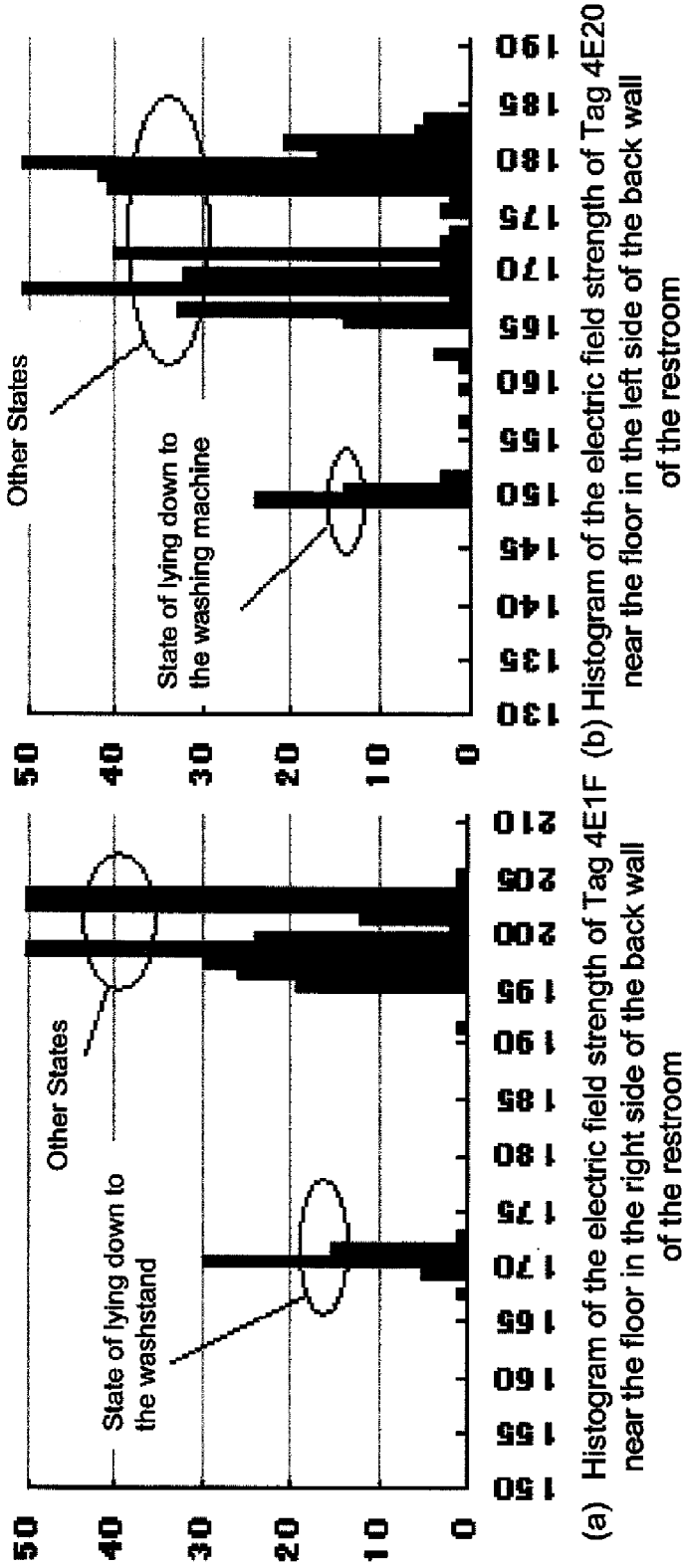
FIG. 6 shows histograms of electric field strength by characteristic extraction means of the object state detection apparatus and method according to the first embodiment of the present invention.

The diagram on the left side of FIG. 4A shows the result of measuring the electric field strength when the tags and the tag reader are provided near the floor and at positions so that a fallen person is positioned between the tags and the tag reader as shown in FIG. 2 and on the right of FIG. 4A. When the still state is captured from the time-series change of the electric field strength by the characteristic extraction means 7 (that is, Equations 1 and 5) and viewed as histograms, the histograms are as shown in FIGS. 6(A) and 6(B). Here, the horizontal axis indicates the electric field strength value, and the vertical axis indicates the number of appearances.

As seen from FIG. 6(A), the electric field strength value of the tag installed near the floor on the washstand side in the still state in which the person lies down on the washstand side can be clearly distinguished from that in other still states. That is, according to object state detection based on the RFID tag system according to the present invention, it is possible to clearly detect a fallen state only by REID tags and a tag reader installed in an environment, without attaching a sensor or the like to a human body, by actively utilizing the fact that the electric field strength of an RFID tag has a characteristic area on a histogram in a still state and the fact that an arrangement of tags exists such that the characteristic area in a still state caused by falling down and the characteristic area in other still states in a closed space can be distinguished from each other. Furthermore, since the fact that the human body itself influences the multi-path of the radio wave is actively utilized, it is not necessary to separately prepare means for shielding radio waves transmitted by the RFID tags in conjunction with change in the motion or state of a person.

The measurement results will be described in detail, from the upper left diagram in FIG. 4A, Eav=202, and the electric field strength value when the person falls down on the washstand side is: E=170. Therefore, the deviation rate is: Edev≅16%. The maximum deviation rate in the states other than the state in which the person lies down on the washstand side is Edev≅5% when E=192. Therefore, in this case, by setting the maximum deviation rate in the normal state to, for example, 10%, it is possible to sufficiently distinguish the normal state from the fallen state. As seen from FIG. 6(B), as for the electric field strength value of the tag provided at the lower left position on the wall opposite to the entrance of the restroom and near the floor, the state in which the person lies down on the washing machine side and lies still can be clearly distinguished from the other still states. In this case, from the lower left diagram in FIG. 4A, Eav=179, and the electric field strength value when the person falls down on the washing machine side is: E=150. Therefore, the deviation rate is: Edev≅16%. The maximum deviation rate in the states other than the state in which the person lies down on the washing machine side is: Edev≅8% when E=165. Therefore, also in this case, by setting the maximum deviation rate in the normal state to, for example, 10%, it is possible to sufficiently distinguish the normal state from the fallen state.

In the above fallen state detection, by causing a fall place to be displayed on the centralized control system in accordance with a fallen state signal from each restroom, it is possible to remotely detect a fallen state of a person who requires nursing care or the like. According to this method, it is not necessary to continuously go around, and the burden on those who are in charge of nursing care for multiple people can be reduced.

The place to which the first embodiment is applied is not limited to a restroom. The first embodiment can be applied to any place if it is a closed space where the possibility that a fallen person can be immediately found is low.

According to the present invention, a characteristic area corresponding to each still state exists on a histogram; the width of the characteristic area becomes very small compared to the width in a motion state; and the respective characteristic areas are significantly separated in accordance with the arrangement of the RFID tags. Therefore, it is possible to clearly detect a fallen state by utilizing this separation of the characteristic areas.

Second Embodiment

An object state detection apparatus and method according to a second embodiment of the present invention will be described with reference to drawings.

Figure 7:
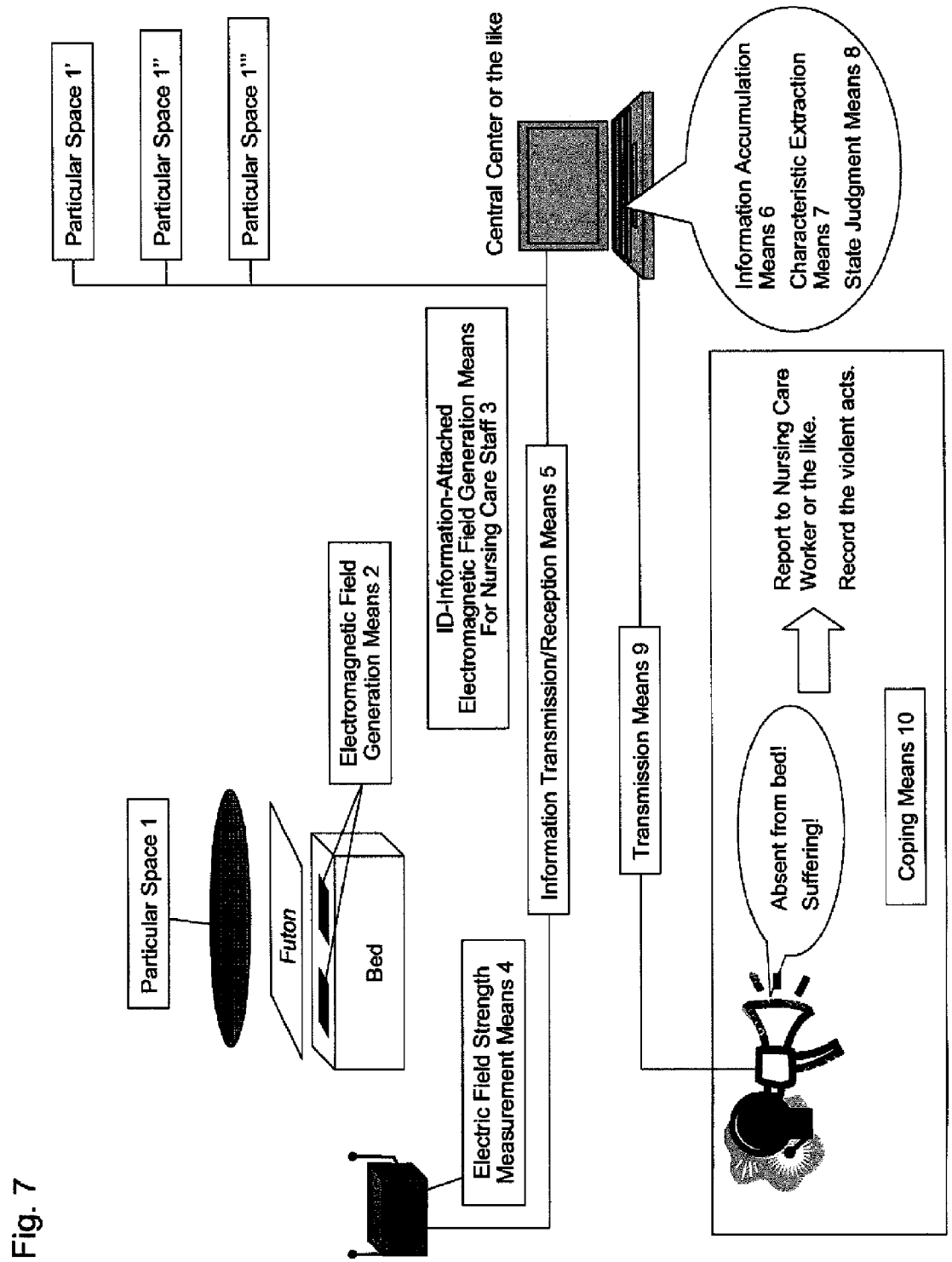
FIG. 7 shows the outline of installation situation when an object state detection apparatus and method according to a second embodiment of the present invention is applied to detection of an absence-from-bed/presence-in-bed state.

FIG. 7 is a diagram showing a detailed installation state of the object state detection apparatus, and at least one ID-information-attached electromagnetic field generation means 2 which is provided near the floor in FIG. 2 is provided under a bed or a futon. The electric field strength measurement means 4 is provided within a range where the electric field strength of the electromagnetic field generation means 2 can be measured and advantageously provided so that the space to be detected is located between the electromagnetic field generation means 2 and the electric field strength measurement means 4. Separately from the electromagnetic field generation means provided under the bed, the ID-information-attached electromagnetic field generation means 3 are prepared for a nursing care staff. The information accumulation means 6, the characteristic extraction means 7, the state judgment means 8, the transmission means 9 and the coping means 10 are not necessarily required to be provided near the particular space 1. They may be provided in a distant space such as in a nurse center, in a control panel room and on an information manager's desk.

Figure 8:
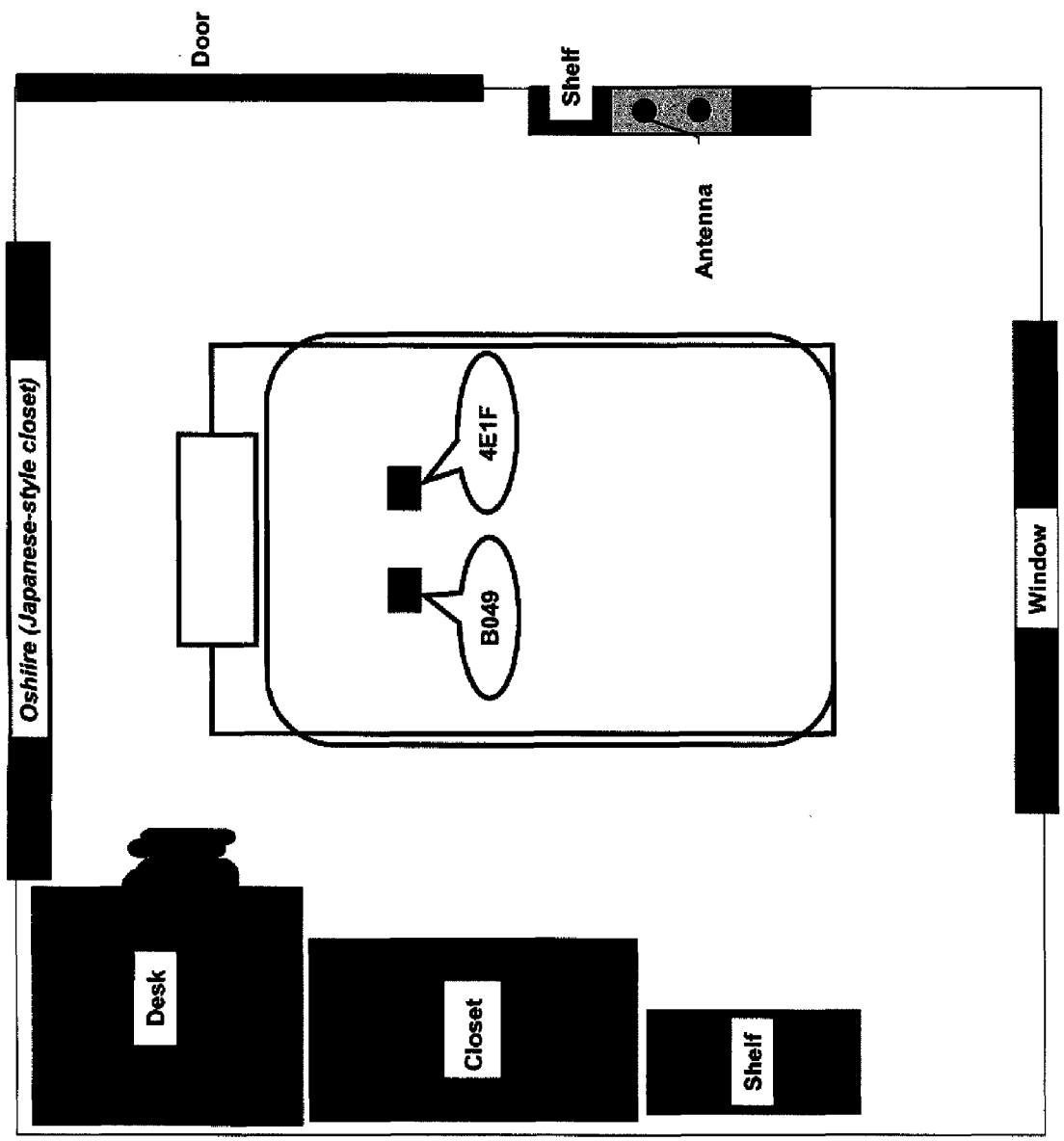
FIG. 8 shows detailed installation situation of a tag and an antenna of the object state detection apparatus and method according to the second embodiment of the present invention.

Now, it is supposed to desire detection of an absence-from-bed state to know wandering. In this case, if the states of Equations 1 and 2 are detected for all the tags, it can be judged that an elderly person has gotten out of bed. By arranging the positions of RFID tags on right and left sides as shown in FIG. 8, the state while in bed can be grasped to some extent. Furthermore, the state in which the elderly person continues moving largely can be extracted by setting a large value for S in Equations 3 and 4. Therefore, it is possible to count the continuing time of this state to detect a case where large fluctuation continues for a long time and detect an abnormal movement such as a movement in the case of the elderly person having a fit and a movement in the case of being cruelly treated.

Figure 9:
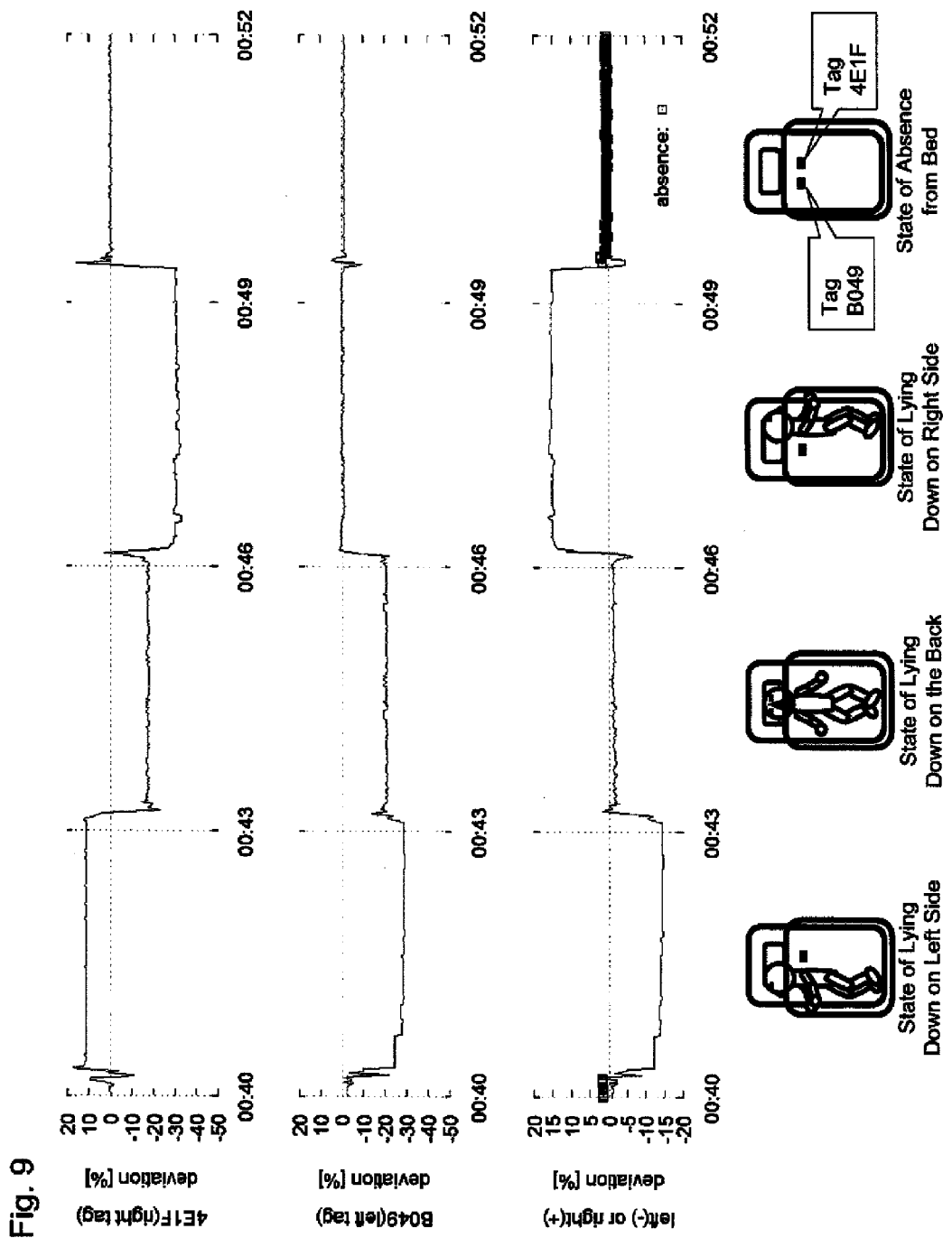
FIG. 9 shows the result of measuring change in the electric field strengths of two RFID tags according to change in the position of a target subject by the object state detection apparatus and method according to the second embodiment of the present invention.

FIG. 9 shows fluctuation of the electric field strength which has been measured by a tag reader in the case where two RFID tags are provided on the tatami mats in an eight-mat room with an ordinary futon spread thereon, and the tag reader is provided on a shelf away from the RFID tags by about 1 m. Here, as shown in the bottom of FIG. 9, a target subject is at a position on the left side of the futon from 00:40 to 00:43; at a position in the center of the futon lying down face up from 00:43 to 00:46; at a position on the right side of the futon from 00:46 to 00:49; and is absent from the futon from 00:49 to 00:52. The top diagram in FIG. 9 shows Equation 7 showing change in the rate of deviation of the electric field strength of the tag (4E1F) provided on the right side from that in the no-person state. It is known that downward deviation exceeding 10% is shown in the state in which the target subject lies down face up and places himself on the tag, and in the state in which the target subject is on the right. The second diagram from the top in FIG. 9 shows Equation 7 showing change in the rate of deviation of the electric field strength of a tag (B049) provided on the left side from that in the no-person state. It is known that downward deviation exceeding 10% is shown in the state in which the target subject lies down face up and places himself on the tag, and in the state in which the target subject is on the left.

Attention is paid to the fact that the electric field strength significantly deviates downward when the target subject places himself on the tag, while upward deviation is ignored. When the magnitude of the deviation rate of the right tag is subtracted from the magnitude of the deviation rate of the left tag, a criterion can be obtained that the difference is plus when the target subject is on the left, minus when the target subject is on the right, and near zero when the target subject is in the center. Furthermore, attention is paid to the fact that, when a human body exists on a bed, a tag provided on the bed shows deviation of 5% or more. By adding the absolute value of the deviation rate of the left tag and the absolute value of the deviation rate of the right tag, a criterion can be obtained that the person is absent from bed if the total value is below 5%. Furthermore, attention is paid to the fact that, when a human body moves on a bed, the electric field strength changes to a degree which can be measured by an existing antenna. The average value of the electric field strength for the past 10 seconds is calculated, and deviation from the average value is calculated. When, for example, 5 points is exceeded, counting is started. When the count exceeds 20, it is assumed that a strenuous movement has continued for 20 periods. Thus, a criterion showing a state in which the target subject on the bed continues thrashing beyond an ordinary range can be obtained.

The third diagram from the top in FIG. 9 shows the above criteria. The solid line indicates which position the target subject exists at. The minus side indicates that the target subject is on the left, and the plus side indicates that the target subject is on the right. The symbol □ indicates that the target subject is absent from of bed. The symbol ○ indicates that an abnormal state continues. Since continuation of an abnormal state does not exist, the symbol ○ is not shown. As seen from this diagram, the states in which the target subject is on the left, in the center, on the right, and absent are very clear.

Figure 10:
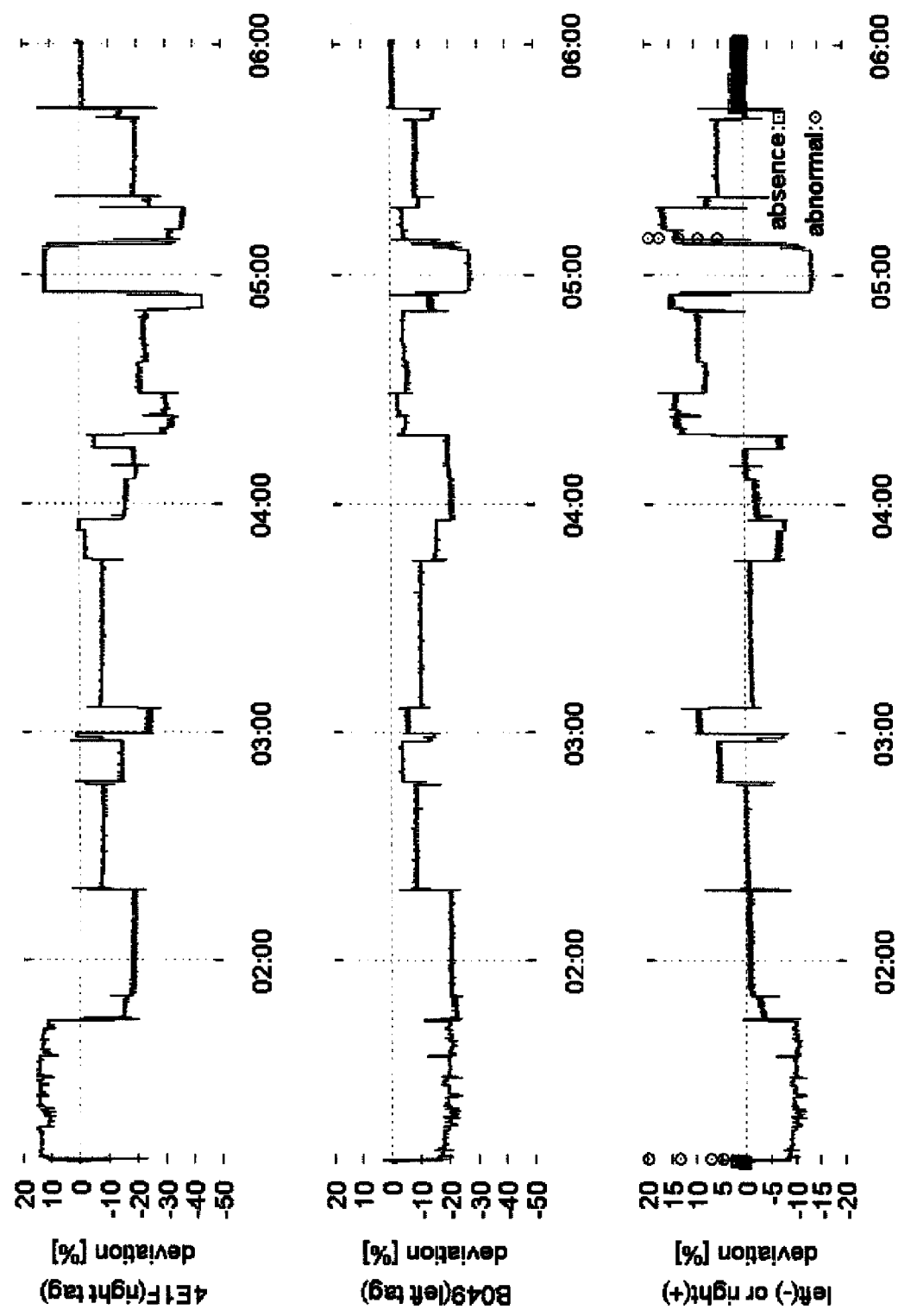
FIG. 10 shows the result of measuring change in the electric field strengths one night by the object state detection apparatus and method according to the second embodiment of the present invention.

FIG. 10 shows a result of continuing this experiment one night. Beginning at the top, the diagrams show the deviation rate of the right-side tag, the deviation rate of the left-side tag, and the result of subtracting the deviation rate of the right tag from the deviation rate of the left tag (plus deviation is assumed to be 0), respectively. Similarly to the above, the absence-from-bed state is denoted by the symbol □, and the abnormality continuing state is denoted by the symbol ○ in the diagram at the bottom. As seen from the diagram at the bottom, since the target subject is not in bed at the beginning of the test, the symbol □, which is an absence-from-bed signal, is shown. Since a strenuous movement continues when the target subject gets in bed, the symbol ○, which is an abnormality continuing state signal, is shown. Though the target subject continues to be at a position of being on the left, he cannot sleep soon and repeats small movements. Before 02:00, he is at a position of being in the center (probably lying down face up), stops the small movements and sleeps. Though he moves at about 03:00, he continues sleeping stably. The movement becomes active as morning comes. After 05:00, the abnormality continuing state signal appears, and he gets out of the futon before 06:00. Here, the threshold for the abnormality continuing state is set to 5 points, and the duration time is set to 20 seconds. It is conceivable that, in the case of violence, a fit, or the like, the movement is more strenuous, and the duration time is longer. Since the parameters are changeable according to the motion to be extracted, it is possible to grasp sleep disorder and the like.

Figure 11:
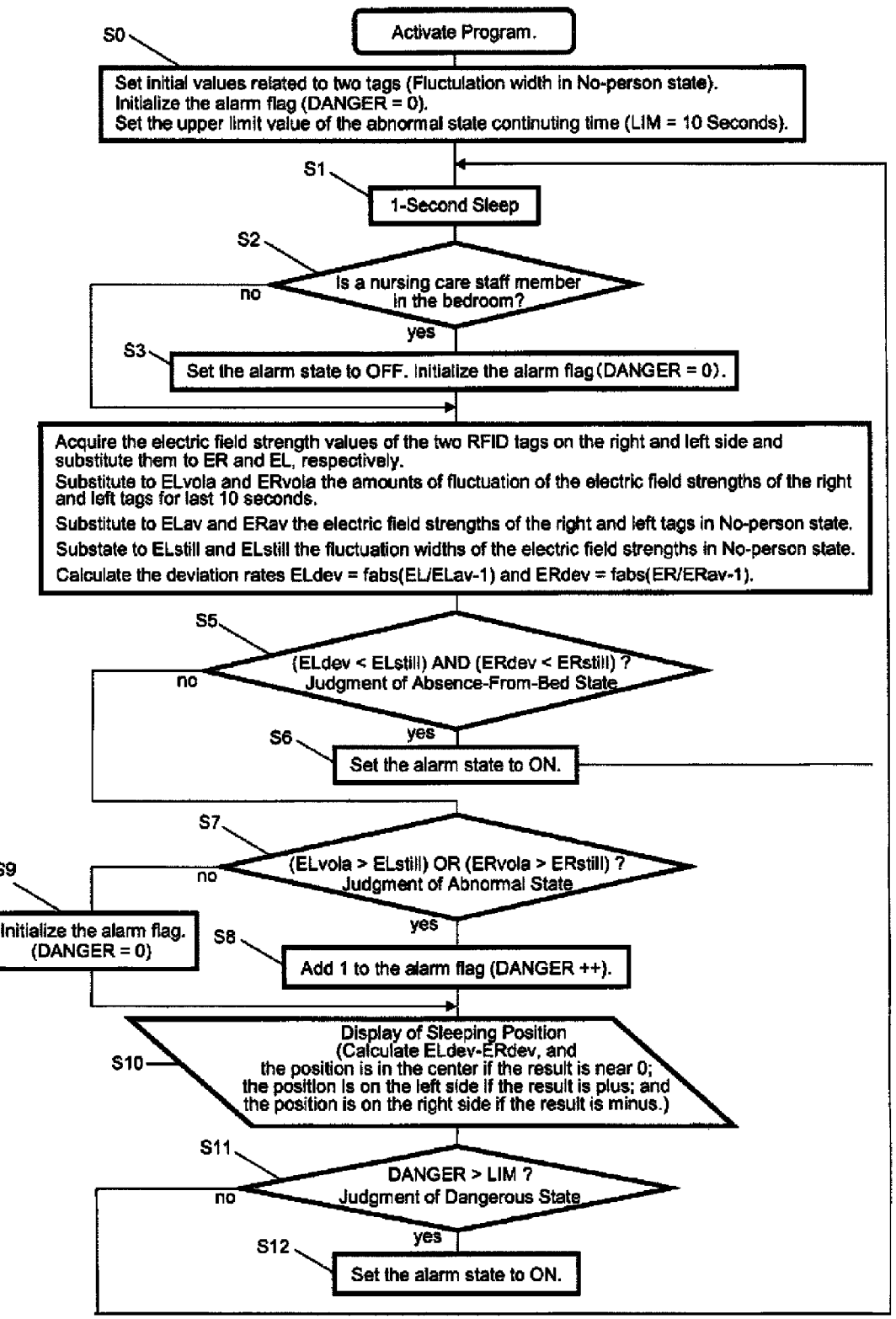
FIG. 11 is a flow diagram showing the operation of the object state detection apparatus and method according to the second embodiment of the present invention.

FIG. 11 shows an example of a basic operation of the absence-from-bed/presence-in-bed state detection system.

0: Two electromagnetic field generation means 2 (RFID tags) provided near the particular space 1 (a position between the floor and the futon which is just under the right and left shoulder blades when the target subject lies down face up) periodically (for example once per second) generate specific ID information as a modulated electromagnetic wave using ASK or FSK, and continue to identify and measure the electromagnetic wave for each ID by the electric field strength measurement means 4. The electromagnetic field generation means 3 are attached to the nameplates or the like of the nursing care staff and also periodically (for example once per second) generate specific ID information as a modulated electromagnetic wave using ASK or FSK, and continue to perform identification and measurement for each ID by the electric field strength measurement means 4. However, since the electromagnetic field generation means 3 is not fixed near the particular space 1, it can seldom perform measurement. Measurement is possible only when a staff member comes close to the site.

1: In a computer or the like which comprises the information accumulation means 6, the electric field strength of two RFID tags arranged on the right and the left near the particular space 1 in the no-person state and its fluctuation, and the upper-limit value of the abnormal state continuing time are set, and the abnormality state detection flag is set to be off (DANGER=0) (step S0).

2: 1-second sleep (step S1).

3: The computer which comprises the information accumulation means 6 checks whether the electric field strength of the electromagnetic field generation means 3 (RFID tag) attached on a staff member could be measured by the electric field strength measurement means 4 (step S2), sets an alarm state to be off if it could be measured (thereby, a siren or the like is stopped), and initializes the alarm flag (DANGER=0) (step S3). If the electric field strength of the tag for a nursing care staff member has not been measured, the alarm mode is kept as it is.

4: The computer which comprises the information accumulation means 6 acquires the electric field strength values of the two electromagnetic field generation means 2 (the right and left RFID tags) from the electric field strength measurement means 4, calculates the average value and the amount of fluctuation for a predetermined period (here, 10 seconds) for each of the electric field strength values, reads the electric field strength of each tag in the no-person state which have been set at step S0 and the fluctuation width, and calculates the rate of deviation from the electric field strength in the no-person state (step S4).

5: Judgment of an absence-from-bed state is performed (step S5). Specifically, if the amount of fluctuation of the electric field strength values of both of the right and left tags for the period of 10 seconds is smaller than the width set in advance, the characteristic extraction means 7 judges the absence-from-bed state (step S5).

6: If the absence-from-bed state is judged to exist, an alarm state is set to be on, and the flow returns to step S1. The alarm state here may be any function for informing a place of the absence-from-bed state, such as a state of turning on and off each passage light, a state of turning on and off each light in a management center and a state of generating an alarm (S6). To release this sate, it is necessary for a staff member to go to the site (step S3).

7: If the absence-from-bed state is not judged to exist, judgment of an abnormal state is performed (step S7). Specifically, if it is judged by the state judgment means 8 that the amount of fluctuation of the electric field strength value of at least any one of the two tags for the past 10 seconds exceeds the fluctuation width set value, the abnormal state is judged to exist (step S7).

8: If the abnormal state is judged to exist, 1 is added to the alarm flag (step S8).

9: If the abnormal state is not judged to exist, the alarm flag is initialized (step S9).

10: The sleeping position and the sleeping state are displayed on the monitor or the like in the centralized control room (step S10).

11: Judgment of a dangerous state is performed (step S11). Specifically, when the abnormal state flag exceeds a value set in advance (here, 20 seconds), the dangerous state is judged to exist (step S11).

12: If the dangerous state is judged to exist, the alarm state is set to be on. The alarm state here may be any function for informing a place where the dangerous state has occurred, such as a state of turning on and off each passage light, a state of turning on and off each light in a management center and a state of generating an alarm. The date and time when the dangerous state occurred is recorded to leave evidence necessary for measures to be taken after the occurrence (step S12).

13: If the dangerous state is not judged to exist, the above procedure 2 is started again. Thereby, vigilant watching performed once per second is realized.

The above function can be performed by a computer for a centralized control system. A microcomputer may be included in the circuit of the electric field strength measurement means 4 so that it is possible to automatically detect the absence-from-bed/presence-in-bed state with high accuracy and issue an alarm according to the state.

Thus, it is possible not only to judge the absence-from-bed/presence-in-bed state but also to grasp the position and movement in bed on a real-time basis. It is necessary only to attach two RFID tags under a futon to realize this. It is not required to attach a complicated measuring instrument to a target subject, and it is not required to prepare a special bed such as a bed with a weighting sensor, either. Naturally, by causing a place where an absence-from-bed state or an abnormal movement continuing state occurs to be displayed on the centralized control system, it is possible to detect a dangerous state of a person who requires nursing care or the like remotely. According to this method, it is not necessary to continuously go around, and the burden on those who are in charge of nursing care for multiple people can be reduced. Furthermore, it becomes possible to extract the frequency of a dangerous state of an elderly person or the like or a violent act, and an important tool for reconsidering a more humane nursing care environment can be provided.

Third Embodiment

Figure 12:
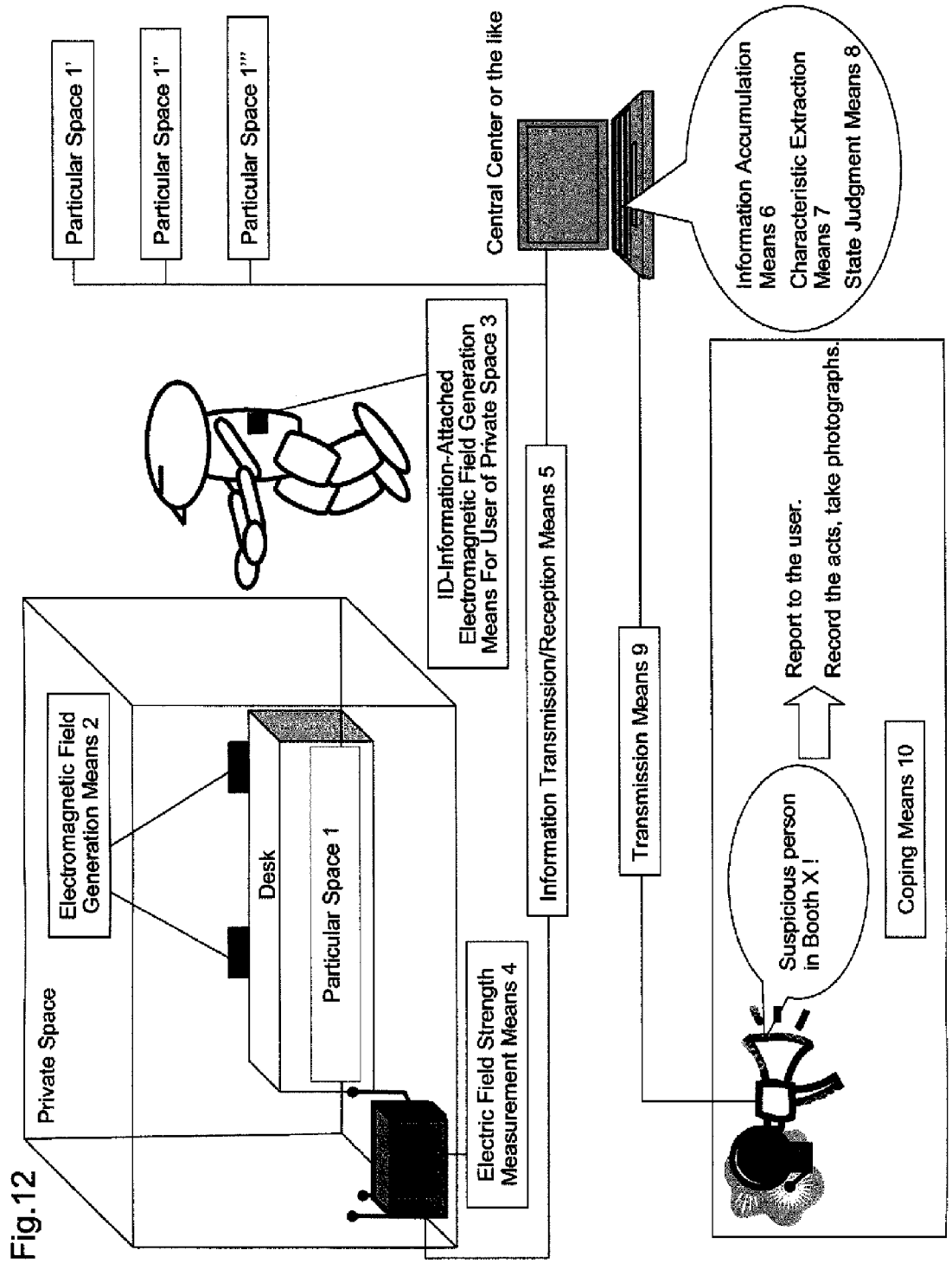
FIG. 12 shows the outline of installation situation when an object state detection apparatus and method according to a third embodiment of the present invention is applied to monitoring of a private space.

The system of the above second embodiment can be applied to continuous remote monitoring of the state inside a room by providing at least one ID-information-attached electromagnetic field generation means 2 in the private space as shown in FIG. 12. In this case, the electromagnetic field generation means 3 to be provided for an individual, for example, a nursing care staff member is provided for the owner of the private space. Thereby, it is possible to monitor and record the acts which a person other than the owner of the private space performs in the space that does not belong to him in a real-time basis. This is because an abnormal state is not detected when the person having the owner ID exists in the space, and alarm means is activated to record movement in the space only when the person is absent.

Figure 13:
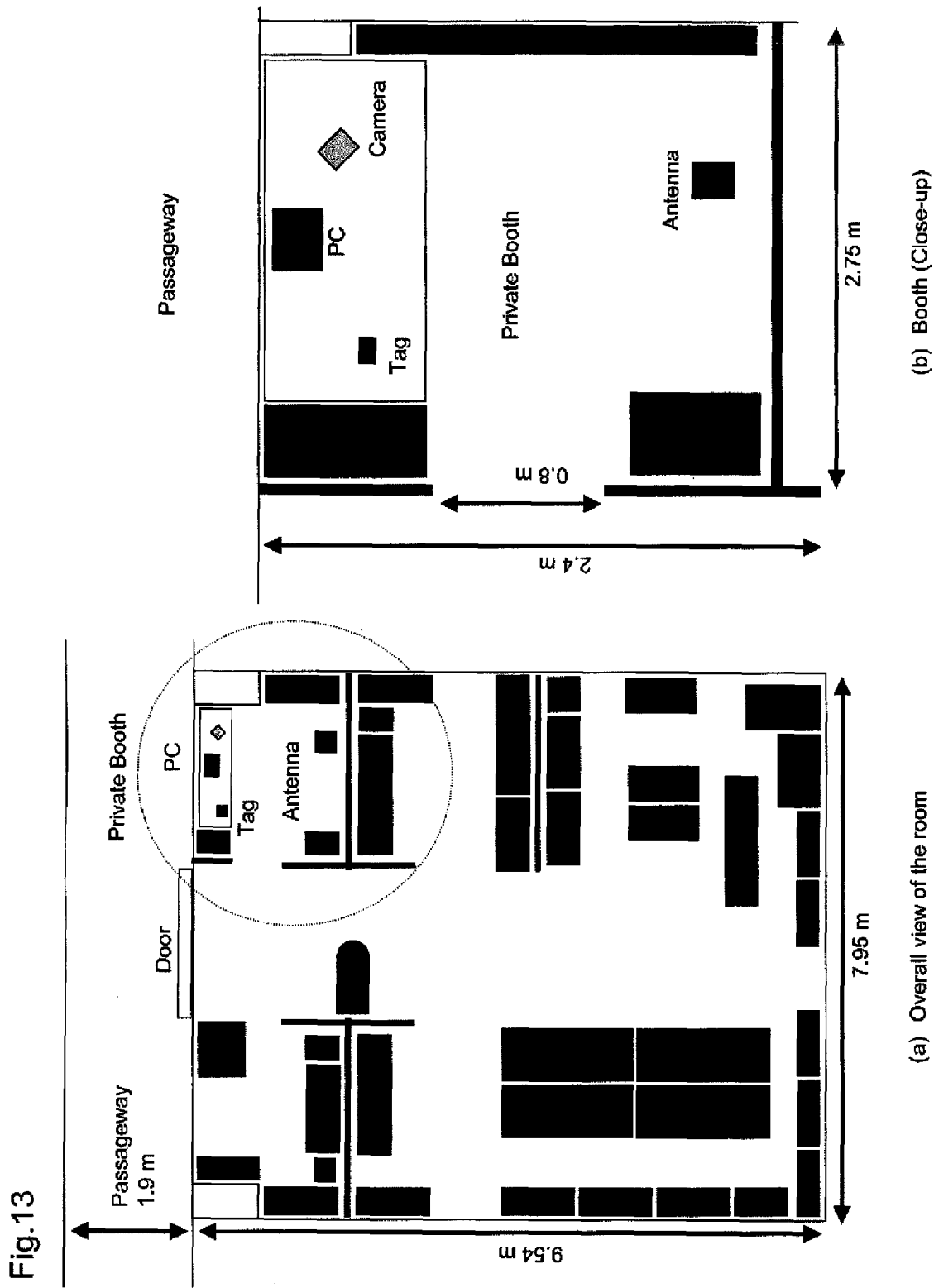
FIG. 13 shows detailed installation situation when the object state detection apparatus and method according to the third embodiment of the present invention is applied to monitoring of a private space.

FIG. 13 shows arrangement of an antenna, a tag and a camera when this system is applied to a personal booth in an office. The tag is attached to the back of a desk calendar. The antenna is provided in a plastic bucket at the back of the booth. The camera is provided in a cup noodle. As the definition of a dangerous state, LIM=0 second is set at step S0 in FIG. 11. The electric field strength in the no-person state is set to 177, and the fluctuation width is set to ±8%. That is, if significant fluctuation of the electric field strength occurs even only for 1 second in the booth when the owner of the personal booth is absent, it is judged to be a dangerous state.

Figure 14:
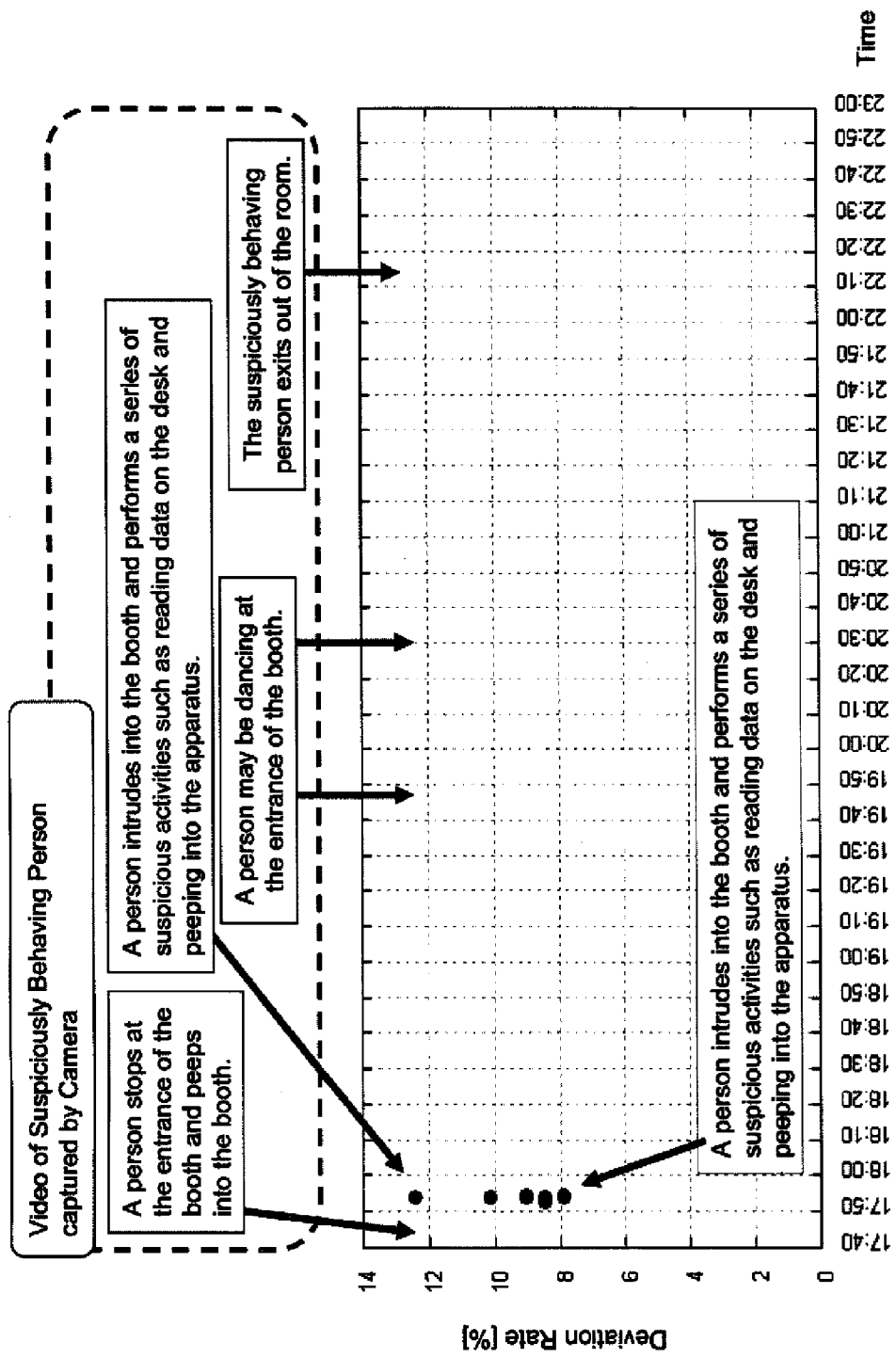
FIG. 14 is a diagram in which the deviation rate of electric field strength measured in a personal booth and a result of recording an intruder by a camera are compared according to the object state detection apparatus and method of the third embodiment of the present invention.

FIG. 14 shows an example of comparison between the deviation rate of electric field strength when a prototype of this system is caused to operate at a particular date and time and the result of recording of an intruder by a camera. As shown in FIG. 14, a signal indicating a dangerous state appears during a certain time zone. As a result of analyzing the video recorded during this time zone, there are a lot of scenes that a person peeps into the booth at the entrance of the booth, but deviation of the electric field strength does not occur. However, only when a suspicious person enters the booth, the dangerous state signal appears.

From the above result, it is known that this system is very effective to state detection of an intruder. Furthermore, it is possible to drastically improve the efficiency of ex post analysis of a security camera and the like. The reason is that, in order to analyze the video taken by a camera, one has to watch unrelated parts until the scene of intrusion is actually reproduced.

In such a whole-time recording method, the percentage of video pictures unrelated to an event concerned is overwhelmingly high, and therefore, the storage medium is wastefully used. Actually, the capacity of the hard disk of the computer is consumed in several days. In order to prevent this, it is useful to specify a part of frames, detect intrusion information from change in pixels, and acquire and store time frames before and after the intrusion event.

According to this, only by adding a simple function of automatically deleting pictures during time zones where a dangerous signal is not issued from this system, it is possible to leave only record of intrusion of a suspicious person, speed up ex post analysis, and efficiently use a storage medium.

Figure 15:
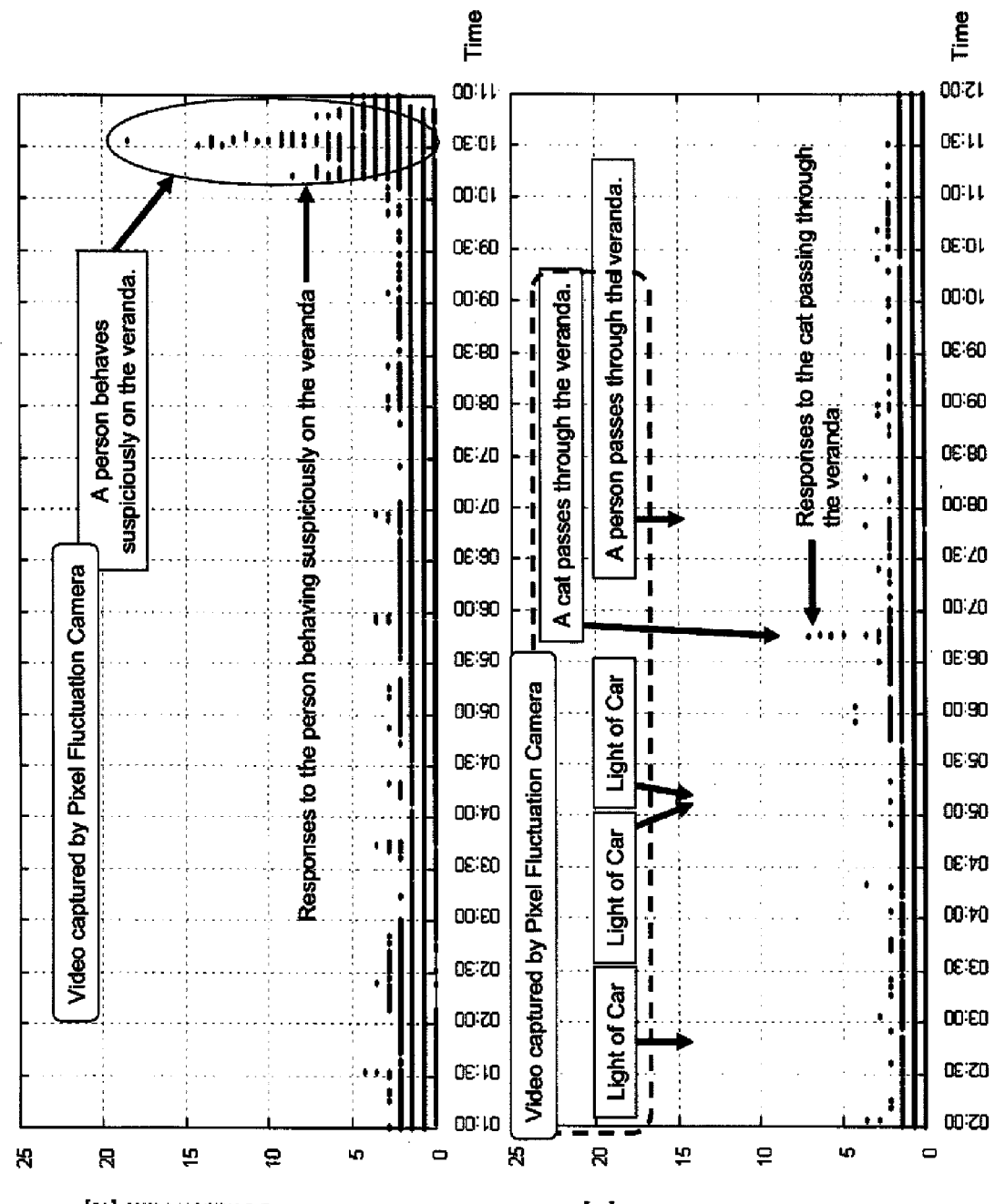
FIG. 15 is a diagram in which changes in electric field strength measured within a veranda and a result of recording an intruder by a pixel change recording camera are compared according to the object state detection apparatus and method of the third embodiment of the present invention.

FIG. 15 shows an experiment result obtained when a pixel change recording camera is provided on a veranda of an apartment and an RFID tag is provided inside the fence of the veranda, in which the times when the camera automatically performs photographing and the result of output of the system of the present invention are compared. Here, the upper and lower diagrams show experiment results for different days. The upper diagram shows an experiment result when a person performed a suspicious behavior on the veranda, and the lower diagram shows an experiment result when a cat happened to intrude into the veranda. In FIG. 14, only signals with a deviation rate of 8% or more are recorded. However, in this experiment, all signals are recorded.

As described with reference to FIG. 15, images of those other than an intruder, such as light of a car or persons walking outside, are recorded in the camera. In comparisons a signal according to this system as described above accurately shows a large deviation rate only when an object (a cat or a person) intrudes. When reaction to a person and reaction to the cat are compared, the deviation rate for the person is much larger than that for the cat, and it continues for a long time. This is because the person performed a suspicious behavior (a peep), while the cat only passed through the veranda. Thus, it is also possible to analyze the intention of a detection target by paying attention to the duration of fluctuation.

On the day of the case shown in FIG. 15, the weather was good, and the number of phenomena recorded in the pixel change recording camera was relatively small. In the experiment result of a windy day, though the number of intruders was zero, more than 50 pieces of video were recorded in the pixel change recording camera because trees and plants were always swaying. It was confirmed that the signal of this system does not react even to such bad weather, and it significantly reacts only to an intruder.

Figure 16:
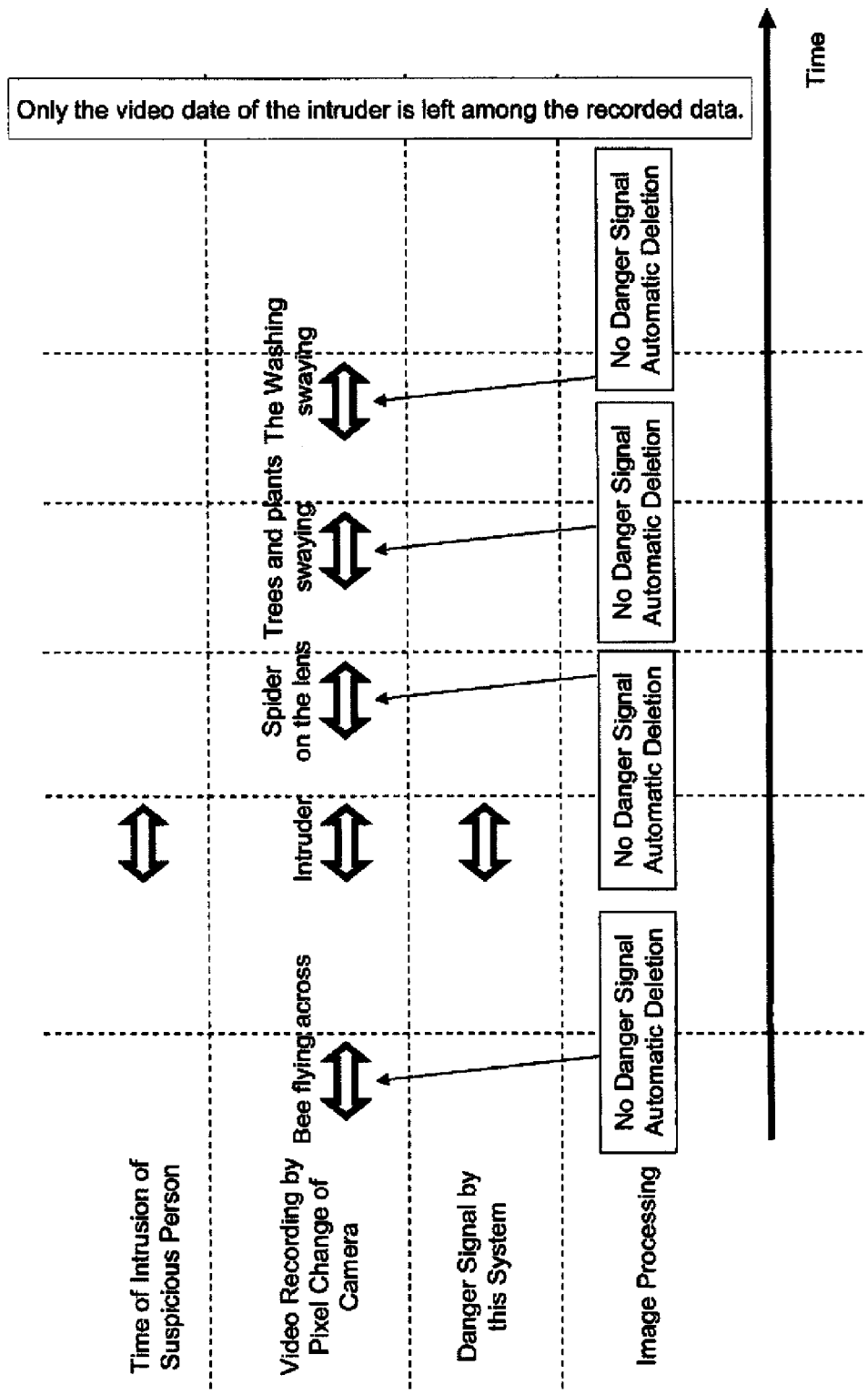
FIG. 16 is a flow diagram showing an effective intruder video storage method and analysis method utilizing the object state detection apparatus and method according to the third embodiment of the present invention.

FIG. 16 shows a summary of the outline of the intruder detection and analysis utilizing the above system. By using the above system, it is possible to capture video of an intruder from camera images/video only when a danger signal, that is, a signal beyond a predetermined deviation rate is obtained and leave the video, and it is possible to dramatically save the storage capacity. Furthermore, it is possible to drastically improve the efficiency of video analysis work for extraction of an intruder. The processing for capturing, recording and the like can be executed, for example, by the coping means 10 in FIG. 12 described above.

Fourth Embodiment

Figure 17:
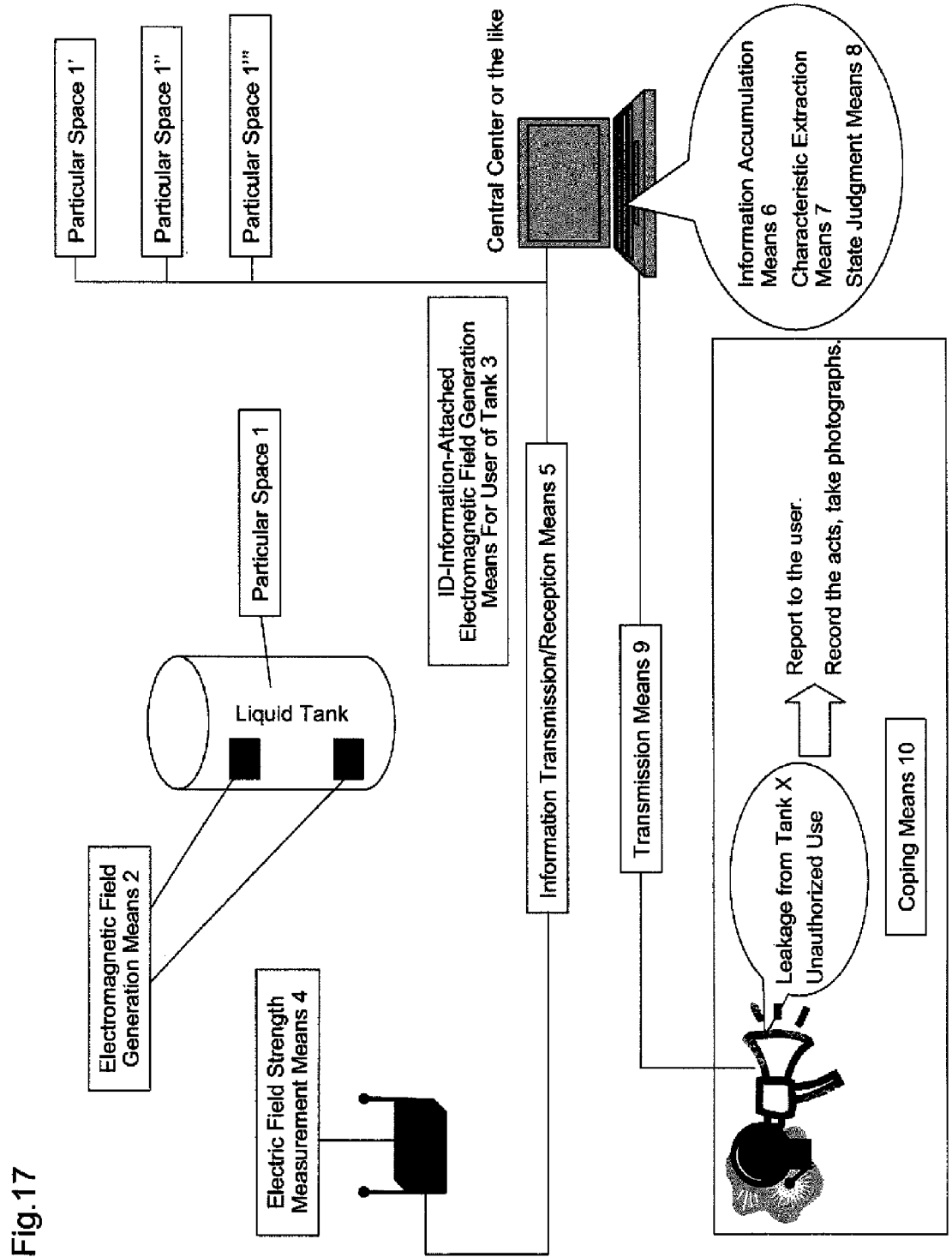
FIG. 17 shows the outline of installation situation when an object state detection apparatus and method according to a fourth embodiment of the present invention is applied to monitoring of leakage of a liquid tank.

The system of the above first embodiment can be applied to continuous remote monitoring of the state of liquid in a container by providing at least one ID-information-attached electromagnetic field generation means 2 on the outer side of the container which contains the liquid as in FIG. 17, and by, in the flow in FIG. 5, determining a new long-term fluctuation amount (for example, a 1-minute fluctuation amount) $E_{long}$ in addition to the short-term fluctuation amount (for example, 10-second fluctuation amount) $E_{vola}$ at step S3 and replacing the conditional statement of step S5 with $E_{long} > E_{still}$. The evidence for that the movement of the liquid in the container can be grasped by the RFID tag attached to the outer surface is the result of measurement of the electric field strength of the RFID tag attached to the outer side of the flush tank of the toilet, which is shown in the second drawing from the top in FIG. 4. As seen from the diagram, when water flows from the flush tank of the toilet, the electric field strength largely changes according to the water level. Here, the important point is the positional relationship among the tag, the antenna and the moving object (water). Though it is proposed to grasp the state by shielding a radio wave in a lot of other methods, the positional relationship here is the order of "antenna-tag-moving object", and the moving object does not shield the radio wave between the antenna and the tag. The existence of a dielectric near the tag (transmitter) influences the radiation efficiency itself and causes such change in the electric field strength. This can be utilized to detect leakage of liquid from a water storage tank for agriculture or a daily life, a fish tank in an aquarium and the like, a fish pool, a fuel tank and the like on a real-time basis.

Figure 18:
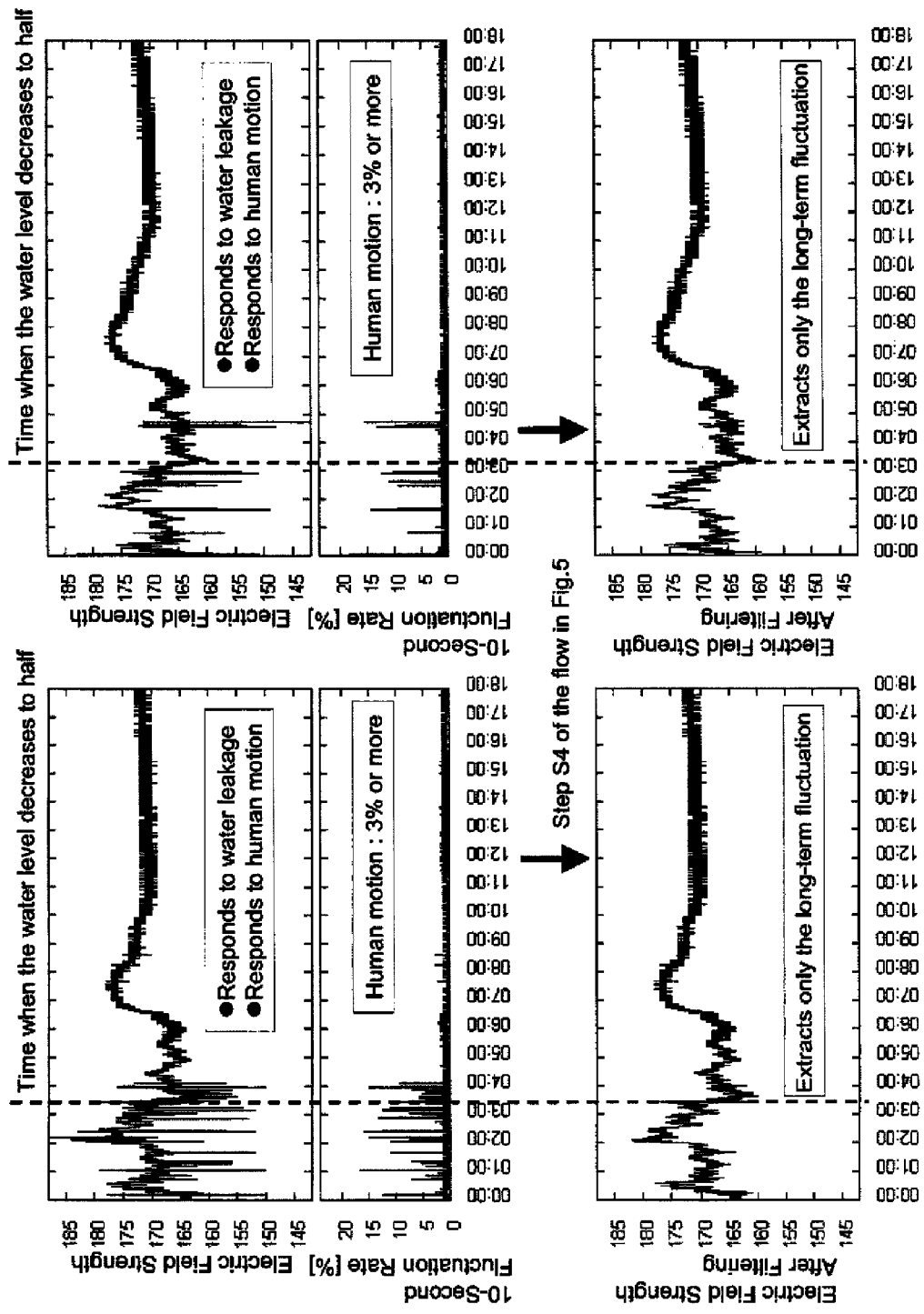
FIG. 18 is a diagram showing changes in electric field strength of an RFID tag installed on a bathtub in a bathroom (upper part), the 10-second fluctuation rate at step S3 of the flow in FIG. 5 (middle part), and changes in electric field strength after removing influence of a human body (lower part), according to the object state detection apparatus and method of the fourth embodiment of the present invention.

FIG. 18 is a diagram in which changes in the electric field strength when one RFID tag is attached to the outer side of a bathtub and changes in the water level in the bathtub are compared. The left and right diagrams show experimental results obtained on different dates and times, respectively, which are presented to confirm reproducibility. In the upper diagrams, it is seen that, since a person frequently enters the bathroom to check the water level in the bathtub from 00:00, the time when the experiment starts, to 05:00, abrupt changes of the electric field strength due to intrusion of the human body are recorded. In the middle diagrams, the calculation result of the 10-second fluctuation rate by step S3 in the flow of FIG. 5 is shown, and it is confirmed that the 10-second fluctuation rate increases when the person enters the bathroom. In the lower diagrams, a result of removing short-term motions by the human body in response to the result of step S3 in FIG. 5. As confirmed from the diagrams, the results of the measurement performed on the different dates and times almost agree with each other. The long-term fluctuation amount $E_{long}$ can be calculated with the use of the data at the lower part. If the period is set to sixty seconds, a 1-minute fluctuation can be extracted, and it is possible to extract a slow fluctuation without being influenced by an abrupt change due to a motion of the human body and the like.

It was very difficult to confirm water leakage by visual inspection because the water leakage was so slow that change in the volume of water could not be recognized within several hours. However, by checking the 1-minute data of the present invention, it is possible to grasp the water leakage. The leakage was due to deterioration of the packing. Thus, by using the present invention, it is possible to find slight leakage of liquid which is difficult for a person to notice, by observation for several minutes.

Fifth Embodiment

Figure 19:
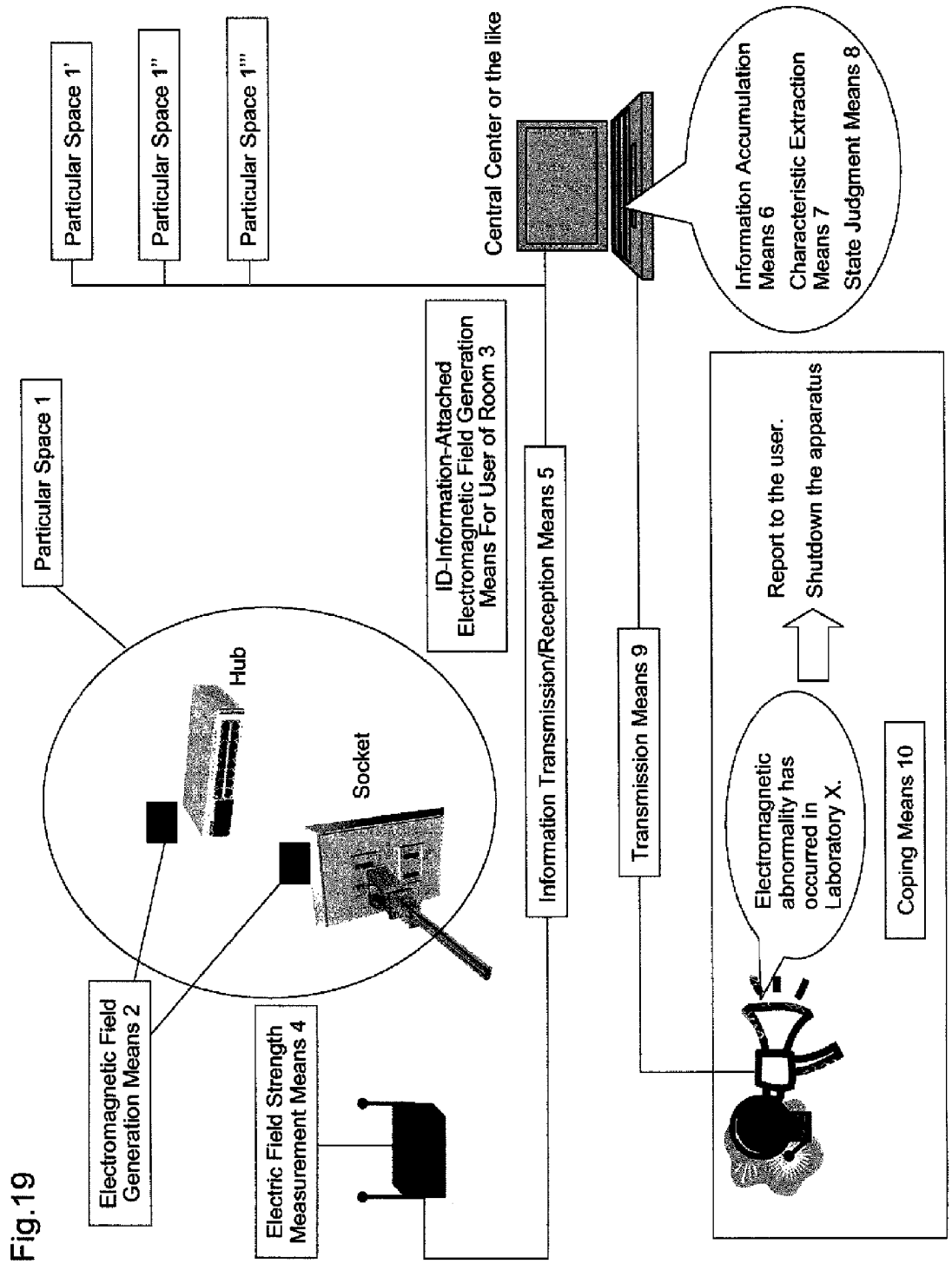

The system of the above first embodiment can be applied to continuous remote monitoring of electrical abnormalities of measurement apparatuses sharing the same electrical wiring by providing at least one ID-information-attached electromagnetic field generation means 2 near a socket or the electrical wiring as in FIG. 19, and by, in the flow in FIG. 5, determining a new long-term fluctuation amount (for example, a 1-hour fluctuation amount) $E_{long}$ in addition to the short-term fluctuation amount (for example, 10-second fluctuation amount) $E_{vola}$ at step S3 and replacing the conditional statement of step S5 with $E_{long} > E_{still}$.

Figure 20:
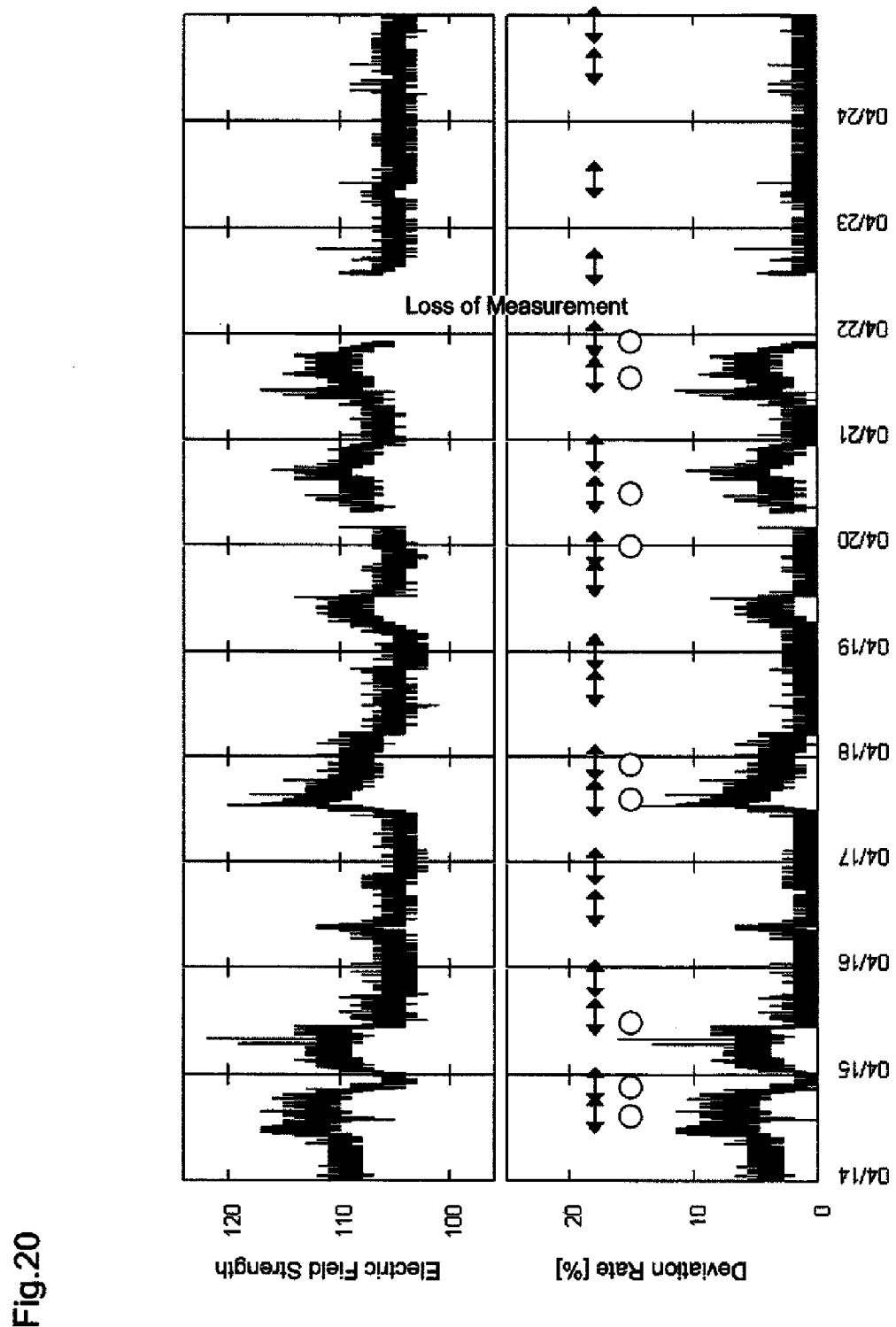
FIG. 20 is a diagram showing changes in electric field strength of an RFID tag installed near a socket (upper diagram) and the absolute value of the deviation rate at step S6 in the flow in FIG. 5 according to the object state detection apparatus and method of the fifth embodiment of the present invention.

FIG. 20 shows changes in the electric field strength when one RFID tag is attached near each of a socket and a hub (upper diagram), and the rate of deviation from a steady value (lower diagram). Here, in the deviation rate graph in the lower diagram, the time periods for measurement by an electromagnetic field measurement apparatus different from the apparatus of the present invention, which is separately prepared and operated during the same period for comparison, are indicated by arrows, and the time periods in which an abnormal measurement value is obtained are indicated by ○. Among 8-hour measurements performed twenty times, an abnormal value is included nine times. As seen from the diagrams, though the deviation rate of the electric field strength of the tag attached near the socket is ordinarily 3% or less, a deviation rate of 5% or more or, further, deviation of 10% or more may be caused though no person enters or exits. Furthermore, it was also known that, while this deviation occurs, an abnormal measurement result is obtained as a value measured by the separately provided electromagnetic field measurement apparatus. More specifically, when the deviation rate is beyond 5%, an abnormal value ○ is measured. Furthermore, the time when other apparatuses within the laboratory ran out of control corresponds to the time of the deviation. Thus, it is possible to grasp an electromagnetic abnormality caused in the socket without touching a cable by using the object state detection method of the present invention.

Sixth Embodiment

Here, a further example will be described. The specifications of an RFID tag and a tag reader used in this example are shown in Tables 1 and 2. In the RFID tag, the battery case of a button battery and surrounding circuits constitute an antenna for outputting radio waves. The tag reader performs diversity reception using two whip-type antennas.

[Table 1]

TABLE 1

Spec of active type RFID tag used.
Active-type RFID tag
(K-ubique ID Corporation, LAS-300T)

| Kind of tag | LAS300T1 |
|---|---|
| Battery Life with transmission interval of 1-second | 7.2 months |
| Range of operating temperature | 0-40° C. |
| Modulation method | FSK |
| Power supply | One button battery (CR2032) |
| Transmission interval | 0.2 seconds, 0.5 seconds, 1 second, 3 seconds, 5 seconds, 7 seconds, 10 seconds, 15 seconds (setting can be changed by jumper; in this experiment, 1 second is set) |
| Transmission frequency | 315.1 MHz |
| Transmission output | Weak radio waves (500 μV/m or less; 3 m method) |
| External dimensions | 47.8 (W) × 28.6 (D) × 8.8 (H) [mm] |
| Mass | Approximately 11 g (including CR2032) |
| Antenna | Also used as button battery case |

[Table 2]

TABLE 2

Spec of active type RFID reader used.
Active-type RFID reader
(K-ubique ID Corporation, LAS-300R)

| The number of tags to be identified | Maximum: 50/sec |
|---|---|
| External IF | RS-232C/LAN (10BASE-T) |
| Receiving frequency | 315.1 MHz |
| Receiving distance | TYP7m |
| Other | Capable of outputting received electric field strength for each tag in 256 stages |
| External dimensions | 152.0 × 116.9 × 30.0 [mm] |

Figure 21:
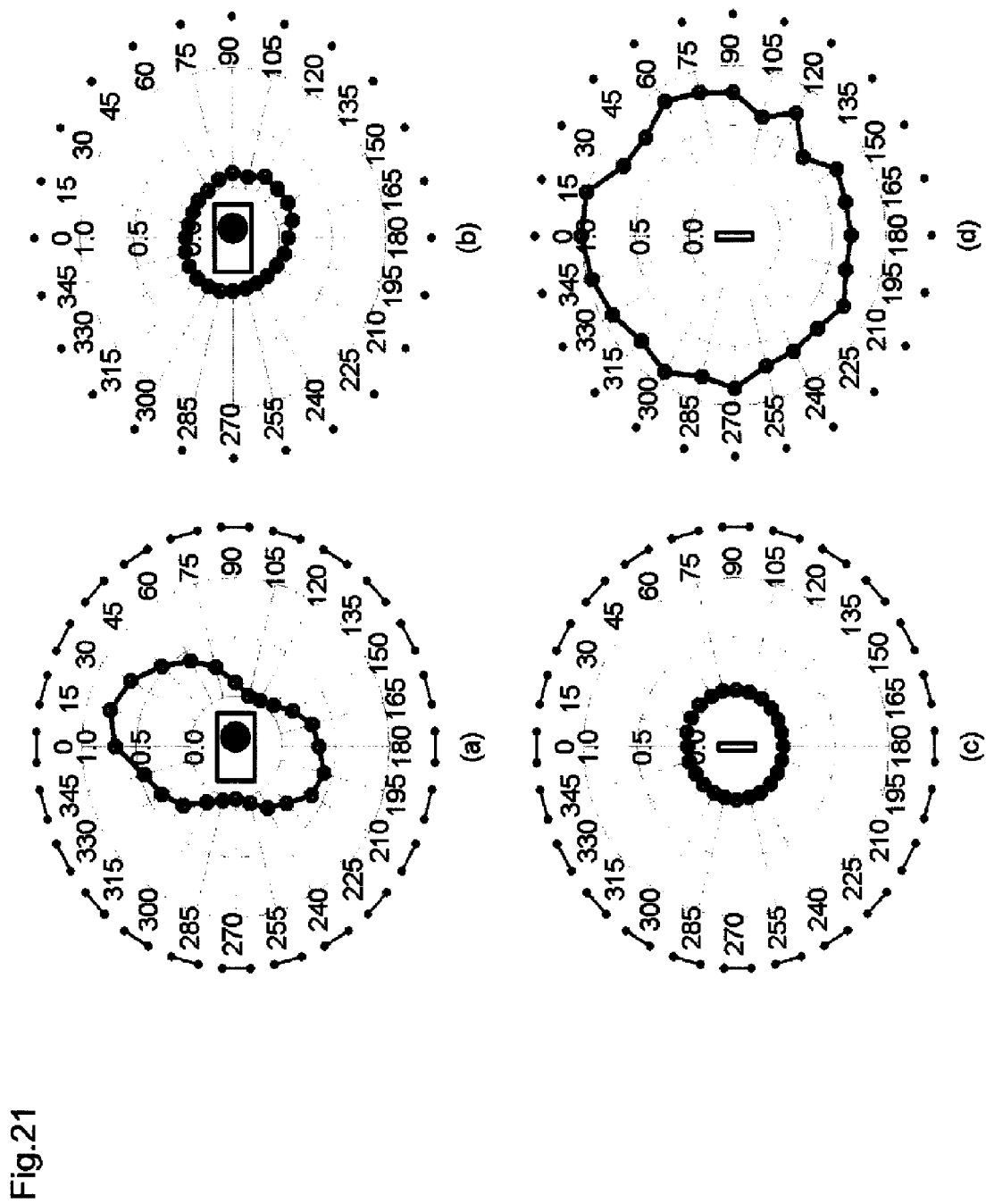
FIG. 21 is a diagram showing radiation characteristics of an RFID tag in a sixth embodiment of the present invention, in which (a) shows detection of a horizontal component when the tag is horizontally positioned, (b) shows detection of a vertical component when the tag is horizontally positioned, (c) shows detection of a horizontal component when the tag is vertically positioned, and (d) shows detection of a vertical component when the tag is vertically positioned.

FIG. 21 shows radiation characteristics of the RFID tag under the above specifications. FIG. 21(a) shows the result of measuring the radiation characteristic of a horizontal component with the dipole antennas which are horizontally positioned at a place away from a tag by 1 m, by installing the tag on a turntable with the battery case on the right side as shown in the center of the diagram and rotating the tag by 15 degrees at a time. Here, the measurement results are shown by polar coordinates. The black circles within the range of radius-direction coordinates 0 to 1 are the measurement values, and the values are connected by a solid line. Normalization by the maximum value of all the measurement values has been performed. As seen from the diagram, the horizontal component of radiated power has a front-back directional characteristic, and there is almost no radiation in the latitudinal direction. FIG. 21(b) similarly shows the result of measuring a vertical component. There is almost no radiation in any direction. FIG. 21(c) shows the result of installing the tag on the turntable with the battery case positioned at the lower side of the tag as shown in the center of the diagram and similarly measuring the horizontal component. There is almost no radiation in any direction. FIG. 21(d) similarly shows the result of measuring the vertical component, and almost equal power is outputted in all directions.

It is originally assumed that this tag is used by being dangled from the neck. It is designed so that radio waves are emitted well in the horizontal direction when it is longitudinally positioned, in order to make it easy to detect the radio waves from a distant place. Since only vertically polarized waves are strong, it is not possible to obtain an electric field strength value in inverse proportion to the distance between the tag and the tag reader if the position relation between the tag and the tag reader changes. Furthermore, it is also conceivable that, by attaching the tag or the tag reader to a human body or a wall, the directional characteristic significantly changes. It is conventionally known that, when the tag is completely surrounded by materials with a large reflection characteristic, its radiation characteristic deviates from the radiation characteristic when it is in free space, due to influence of multiple reflections. However, when observing the changes in the electric field strength caused by different postures of a person in a closed space, these points will not be any bottlenecks, but rather they will be advantages.

Figure 22:
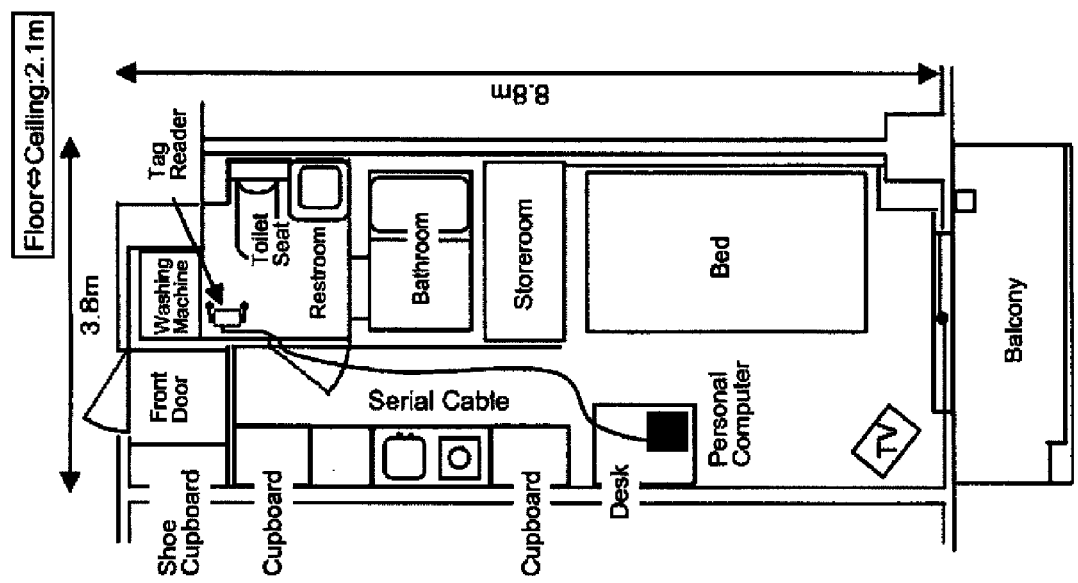
FIG. 22 is a diagram for illustrating a space in which the RFID tags and a tag reader in the sixth embodiment of the present invention are installed.

Under an environment with the room arrangement shown in FIG. 22, the RFID tags and the tag reader are provided in the restroom, which is a closed space, and a data acquisition computer is provided on the desk. The external surface of the washing machine provided in the restroom is made of metal, and metallic materials are also used inside the bathroom adjacent to the restroom. The door of the bathroom is made of nonmetal except for the frame.

Figure 23:
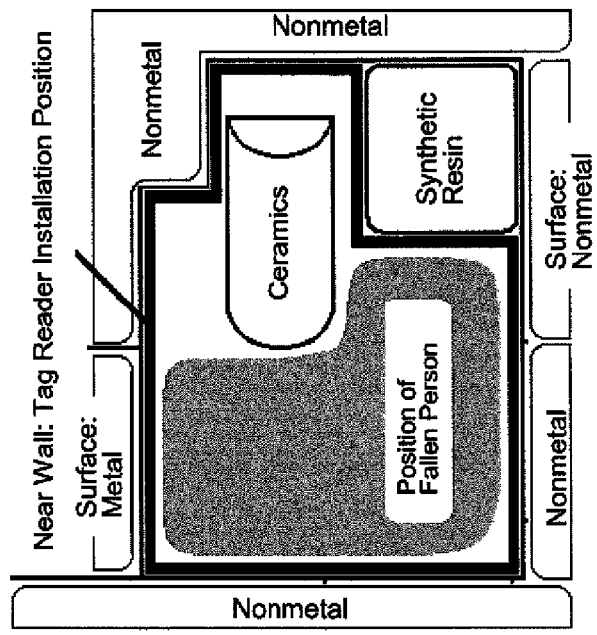
FIG. 23 is a diagram for illustrating the outline of materials constituting a restroom in which the RFID tags and the tag reader in the sixth embodiment of the present invention are installed.

The outline of materials constituting the restroom is as shown in FIG. 23. It has been conventionally suggested that an increase in the communication capacity due to the effect of multiple reflections, or localization of electromagnetic waves beyond a diffraction limit are caused in such an environment with many scattering sources.

Figure 24:
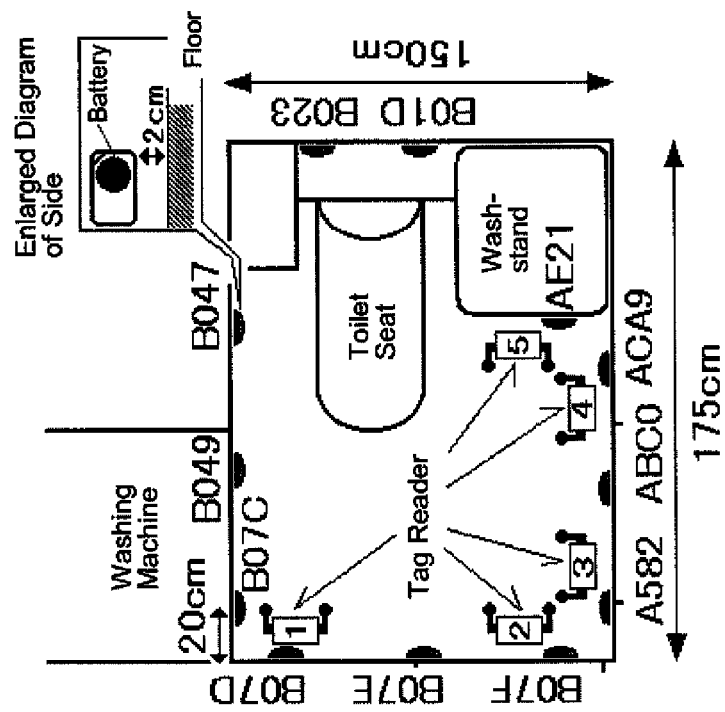
FIG. 24 is a diagram for illustrating arrangements of the RFID tags and the tag reader in the sixth embodiment of the present invention in the restroom.

FIG. 24 shows an arrangement of the RFID tags and tag reader. The devices are provided at the corners or edges of the room in consideration of reducing influence on the living space as little as possible. Here, twelve tags are attached to the wall inside the restroom at 2 cm above the floor with double-sided tape in a manner that the battery (also used as an antenna) is on the right side when seen at a position facing the wall (see the enlarged diagram on the upper right of FIG. 24). As for the lateral-direction arrangement relation among the tags, one tag is attached at each of the positions at 20 cm from the right and left corners of the room, and then one more tag is attached at the middle point between the attached tags. Therefore, the interval between the tags on the same wall plane is about 50 cm. One tag reader is used. First, the position of the tag reader is changed from Position 1 to Position 5 in FIG. 24 in the order of the numbers to measure the electric field strength.

Figure 25:
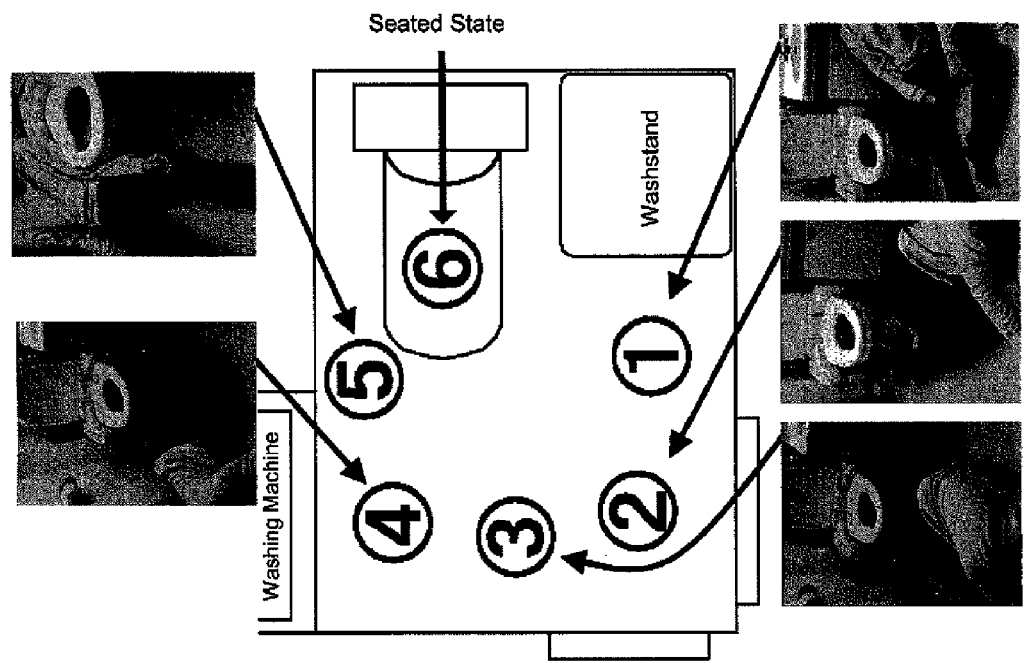
FIG. 25 is a diagram for illustrating fallen states in the restroom in the sixth embodiment of the present invention.

FIG. 25 and Table 3 show examples of assumed still states in the restroom. Fallen states 1, 2, 3, 4 and 5 in the diagram and the table are distinguished from other still states 0, 6, 7, 8 and 9 to detect a fallen state. Here, the distinction between the still states 0 and 6 and the fallen states 1, 2, 3, 4 and 5 will be described first.

[Table 3]

TABLE 3

Assumed still states

| State number | Posture in still state |
|---|---|
| 0 | No one in the restroom |
| 1 | Fall down toward the washstand (FIG. 6①) |
| 2 | Fall down toward the bathroom door (FIG. 6②) |
| 3 | Fall down toward the door (FIG. 6③) |
| 4 | Fall down toward the washing machine (FIG. 6④) |
| 5 | Fall down between the toilet bowl and the wall (FIG. 6⑤) |
| 6 | State of sitting on the toilet bowl |
| 7 | State of standing in front of the toilet bowl |
| 8 | State of standing in front of the washstand |
| 9 | State of standing in front of the washing machine |

After the RFID tags and the tag reader are fixedly arranged, 30-second electric field strength measurement is performed for one still state, and the data of the twelve RFID tags are acquired from the tag reader once every two seconds. For one tag, fifteen or less data is obtained. The reason for the number of data being fifteen or less is that the electric field strength data disordered when the posture changes from a still state to another still state is removed. That is, the electric field strength in a motion state is removed by a filter.

Figure 26:
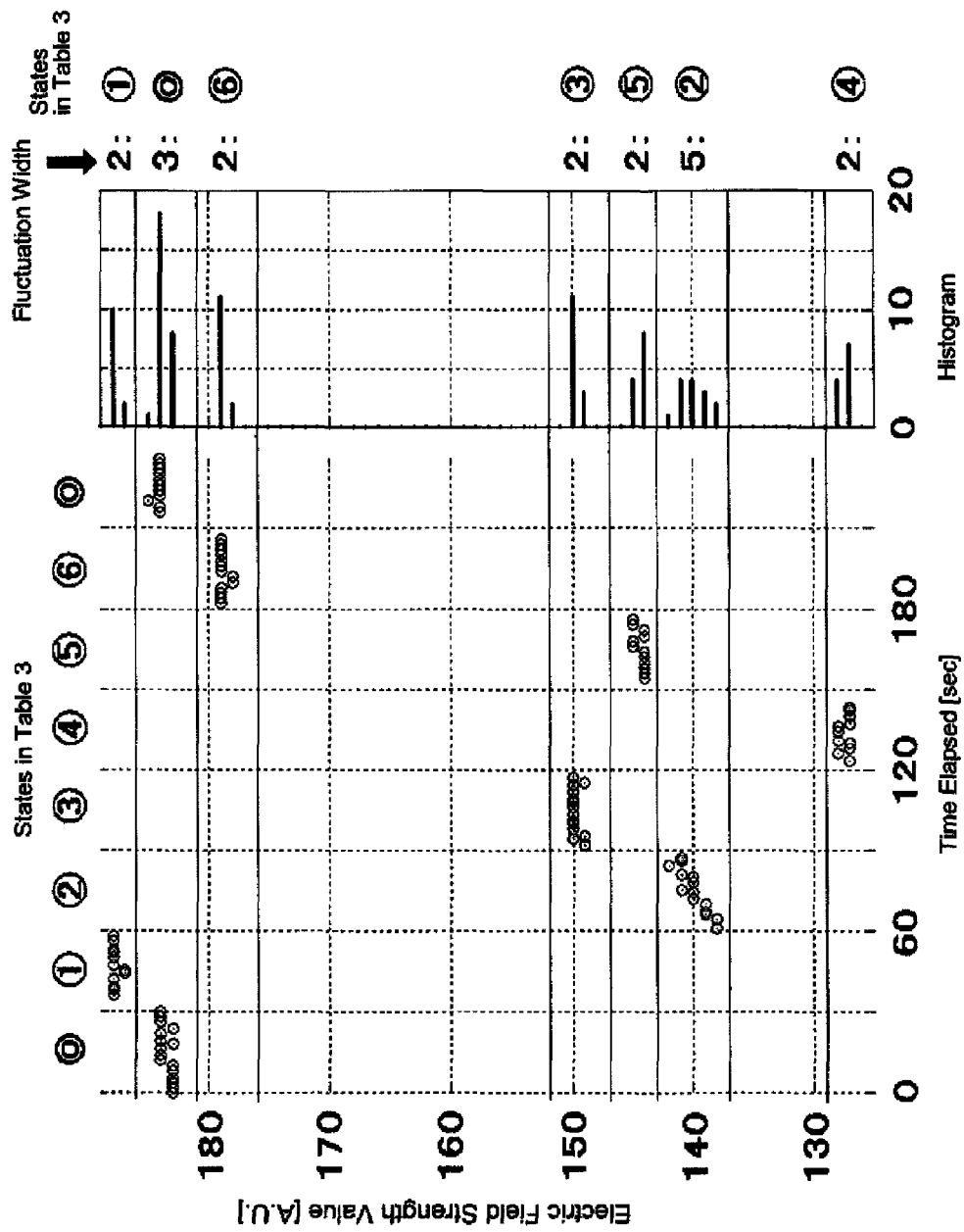
FIG. 26 is a diagram showing temporal changes in the electric field strength and an appearance frequency of the electric field strength values in the sixth embodiment of the present invention.

FIG. 26 shows temporal changes in the electric field strength of a tag ACA9 when the tag reader is provided at Position 1 in FIG. 24. Here, black circles indicate measurement values, and a histogram diagram representing the frequency of the measurement values is shown on the right at the same time. Here, a person with a height of 177 cm keeps a still state for about thirty seconds in each of Postures 1, 2, 3, 4, 5, 6 and 0 in Table 3 in that order and quickly takes the next posture. Disorder of the electric field strength during a motion is removed. As seen from the diagram, an almost constant electric field strength value is shown in all the still states. As can be confirmed from the histogram also, the electric field strength is within the range of ±2 of the peak value corresponding to each state. Only in the state 2, the fluctuation is 5, which is a relatively large value. The reason is presumed to be that the person moved his arm slightly to see a stopwatch to measure thirty seconds. Furthermore, as seen from the diagram, a value as much as 10% lower than the value of the normal states 0 and 6 is stable in the fallen states 2, 3, 4 and 5. Therefore, by setting a threshold, the fallen states 2, 3, 4 and 5 can be easily detected.

Especially, the nature of the still state having the electric field strength almost constant was confirmed for all the tags without an exception.

In the description below, a peak on a histogram corresponding to a still state will be called a stable value of electric field strength, and the width of fluctuation from the stable value will be called a characteristic area.

In a closed space such as a restroom, the rate of the no-person state is high. Therefore, if the devices are provided for a sufficiently long time, the electric field strength in the no-person state is counted most frequently. Here, the stable value of the no-person state is regarded as a reference value, and a deviation rate E is defined by the following equation:

$$E = 100 \times (1 - Ei/E0)$$

Here, Ei denotes the stable value of the 1-minute electric field strength measured by the tag reader when Postures i=1, 2, 3, 4, 5 and 6 in Table 3, and E0 denotes the stable value of the electric field strength when No-person state i=0. In the case of FIG. 26, the deviation rate of the states 0, 1 and 6 is below 10%, and the deviation rate of the states 2, 3, 4 and 5 is 10% or more. That is, according to the data of this tag, it is possible to detect at least the fallen states 2, 3, 4 and 5 by setting the deviation rate to 10%.

As a result of examining the above point for all the twelve tags, it was found that, first, if the tag reader is at Position 1 in FIG. 24:

the tag ABC0 detects the fallen states 2, 3, 4, and 5 when the deviation rate is −10% or below (the deviation rate in a seated-on-toilet-seat state is −3%); and the tag ACA9 detects the fallen states 1, 2, 3 and 4 when the deviation rate is −10% or below (the deviation rate in a seated-on-toilet-seat state is +2%).

That is, by using two tags, it is possible to detect a fallen state while distinguishing it from a seated-on-toilet-seat state.

Figure 27:
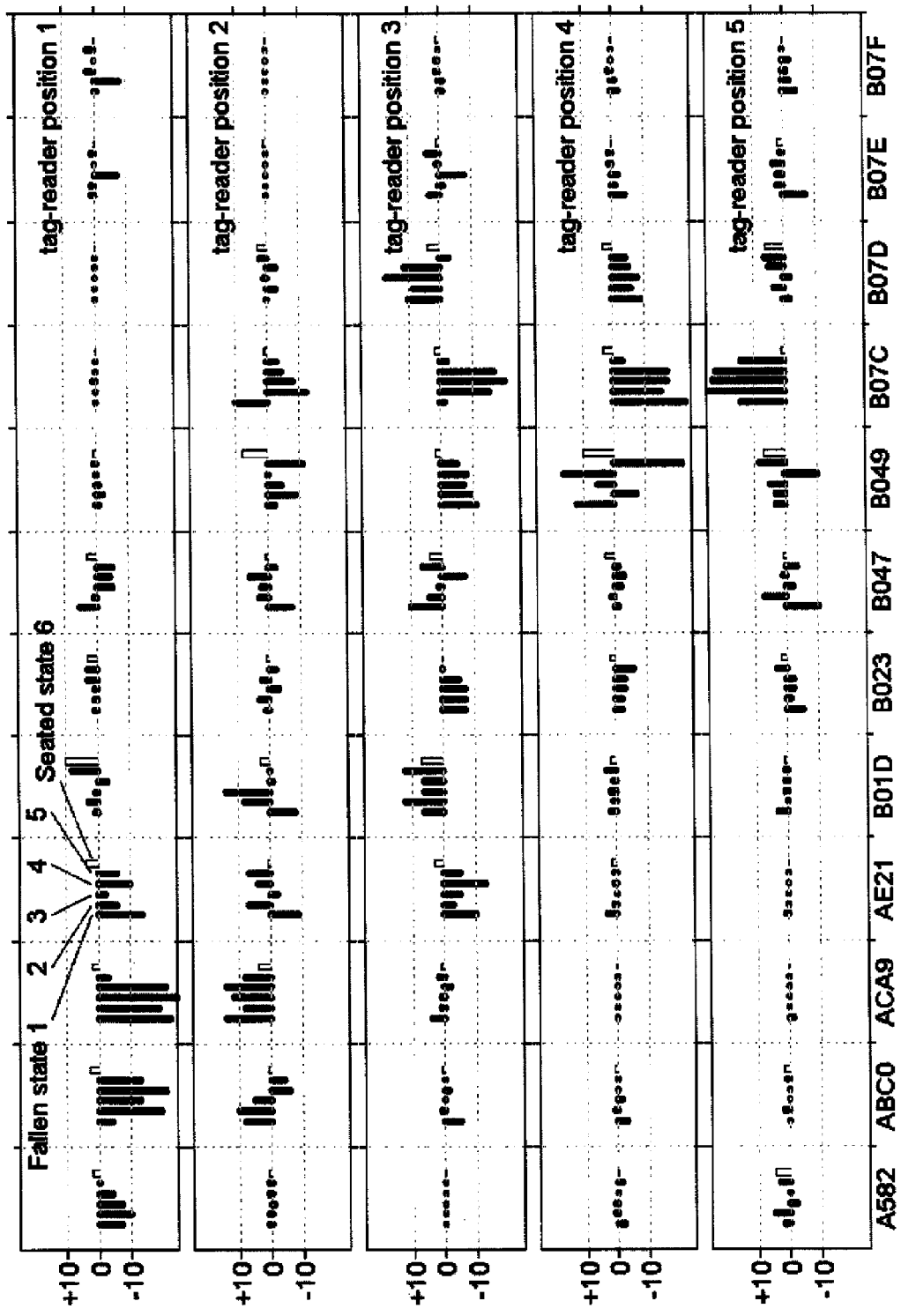
FIG. 27 is a diagram showing the rate of deviation from the electric field strength in a no-person state in the sixth embodiment of the present invention.

FIG. 27 shows the deviation rate of the electric field strength of the twelve tags for the five kinds of installation positions (FIG. 24), for the six kinds of installation states (Table 3). To view the diagram with regard to one tag reader, a line is to be viewed. To view the diagram with regard to each tag, a column is to be viewed. In each column, deviation rates for the still states 1, 2, 3, 4, 5 and 6 are shown as a bar graph in that order. For the fallen states 1, 2, 3, 4 and 5, black bars are used. For the seated state 6, a white bar is used. These bars indicate that, as the value is close to 0, the electric field strength is close to the electric field strength of the no-person state. It is also indicated that, as the white bar is short and the black bars are long, or when the black bars and the white bar are in vertically opposite directions, it is easy to distinguish a seated state and a fallen state.

As seen from this diagram, when the tag reader is at Positions 1, 4 or 5 in FIG. 5, that is, when the tag reader is near the metal wall, the contrast between the deviation rates of a fallen state and a normal state is large. As the number of tags is increased, it is possible to identify a fallen state when the tag reader is at any of Positions 1 to 5. Furthermore, in such a position relation between the tags, the tag reader and the fallen object that the deviation rate is large, the fallen object does not necessarily exist on the line connecting the transmitter and the receiver. The point to be especially noticed is that even if there is a fallen object between the transmitter and the receiver, the radio waves are not shielded, rather they are enhanced.

Figure 28:
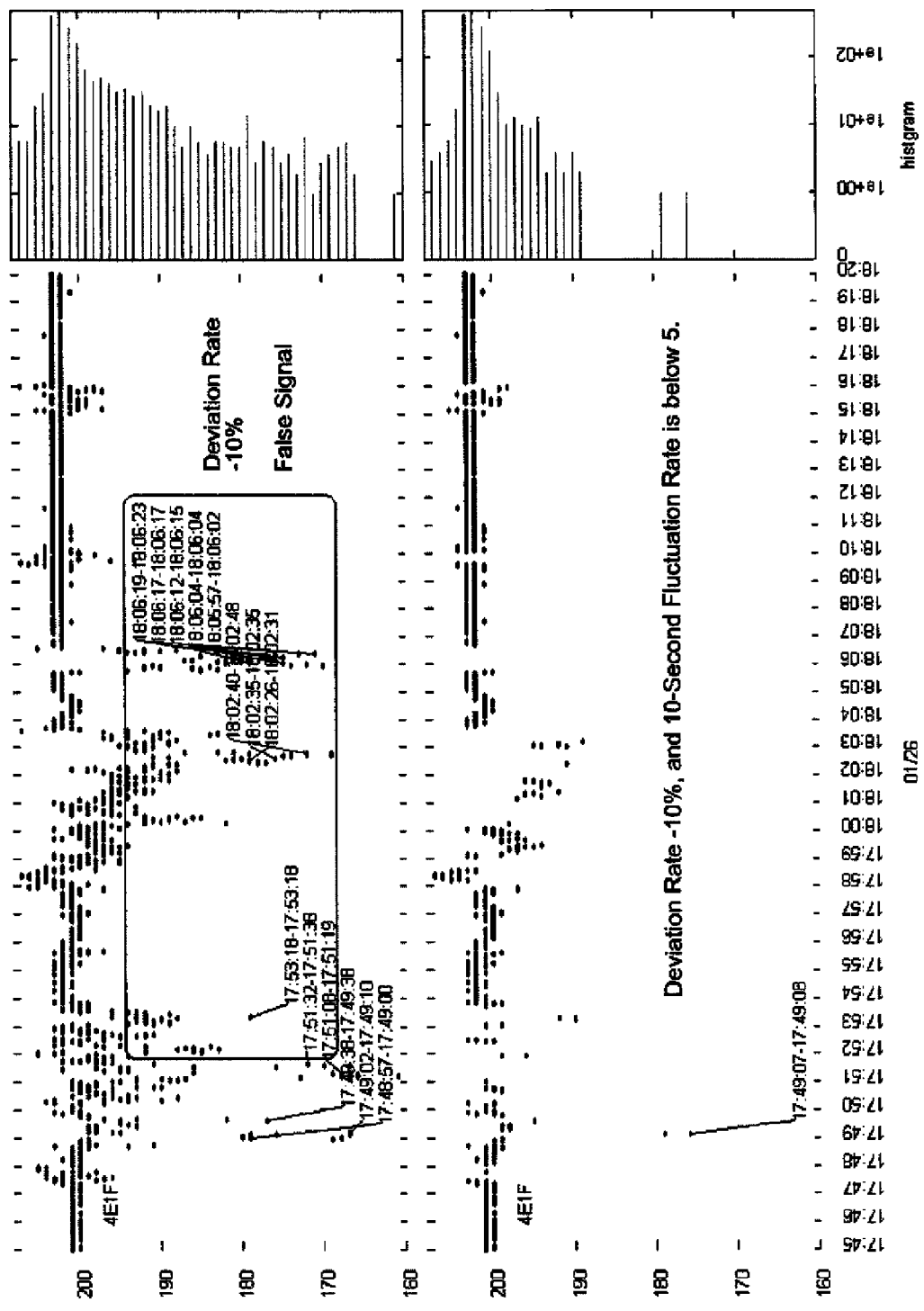
FIG. 28 is a diagram temporal changes in the electric field strength and an appearance frequency of the electric field strength values, when motion states are included, in the sixth embodiment of the present invention.

The upper diagram in FIG. 28 shows temporal changes in the electric field strength with motion states included and also shows its histogram. Examinees were instructed to behave freely and fall down toward the washstand only once when they are alone in the restroom. The notes shown in the diagram indicate the time periods during which the deviation rate is beyond −10%. The installation position of the tag is the position of the tag ACA9 in FIG. 5, and the installation position of the tag reader is the position in FIG. 1. As seen from the upper diagram, the deviation rate is below 180, which is the electric field strength with a deviation rate of −10%, during a total of fourteen time periods. Since the number of falls is 1, the fall detection success rate is $\frac{1}{14} = 0.07$. Furthermore, as seen from the histogram, since the characteristic areas overlap with one other, separation of the states cannot be confirmed. Thus, the motion states include a great number of states with a deviation rate beyond −10%.

Here, it should be noticed that a state of a person having fallen down and being unable to move is a still state. The nature of the electric field strength in a still state is that a stable value and a characteristic area are maintained for a certain length of period. Now, it is assumed that the fluctuation width of a still state is 5 and that the person is in a dangerous state when a state of being unable to move continues for ten seconds. This parameter is determined according to the situation of the spot. In the demonstration of falling down, the examinee lay down for only about ten seconds and thus such a short value was used. The conditional equation can be expressed as follows:

$$\max[E(t)] - \min[E(t)] < 5$$

wherein t denotes any continuous ten seconds, max and min denote to select maximum and minimum) values of the electromagnetic field strength in any continuous ten seconds.

The lower diagram in FIG. 28 shows the result of newly imposing the above conditional equation to the upper diagram. As confirmed from this diagram, only a fallen state can be detected. Furthermore, as seen from the histogram, only the characteristic area of the fallen state is separated from other states.

As appreciated from the above, in order to detect a fallen state, a still state should be extracted from the above conditional equation, and the deviation rate threshold should be set to −10%. The arrangement and the number of the tags and tag readers depend on the size of a closed space and the materials constituting the closed space, and it is necessary to set an appropriate deviation rate threshold. However, by following the procedure described above, it is possible to determine such an arrangement and threshold in a relatively short time. Especially in a nursing-care facility or a hospital in which there are a lot of rooms with the same room arrangement, there is a high possibility that the installation positions in the lot of rooms can be determined by performing calibration once. Furthermore, it can be thought that, if the characteristic area of the no-person state is automatically learned, and a motion state is detected from the negation of the above conditional equation, it is possible to immediately construct detection of a suspicious person in a closed space such as a safety room or detection of a moving body in a corridor or a passage at site, because calibration of a fallen state is unnecessary.

What is claimed is:

1. An apparatus for detecting a state of an object, comprising:
    m (m>=1) electromagnetic field generators provided near a space, the space being occupied by the object when the object is in a particular state;
    n (n>=1) electric field strength measurement devices for identifying and measuring electric field strength which occurs from each of the m electromagnetic field generators; and
    at least one processor configured to calculate characteristics from time-series data of m×n electric field strength and to identify, by statistical processing, the state of the object from the characteristics and characteristic data collected in each of a plurality of still states of the object, wherein the at least one processor is configured to learn an upper-limit value and a lower-limit value of the electric field strength for each time-series data based on the characteristic data of each still state which has been collected, and wherein the at least one processor is configured to identify the state by the fact that input characteristic data is between the upper-limit value and the lower-limit value of the electric field strength or to identify the state by the fact that input characteristic data is not between the upper-limit value and the lower-limit value of the electric field strength, the input characteristic data being time-series data comprising the amount of fluctuation of the time series data of the m×n electric field strength for a predetermined period.

2. The object state detection apparatus according to claim 1, wherein each of the electromagnetic field generators has an antenna structure for controlling spatial distribution of accumulated fields.

3. The object state detection apparatus according to claim 1, wherein an efficiency of radiation of an electromagnetic field into free space by the electromagnetic field generators changes when an object exists nearby.

4. The object state detection apparatus according to claim 1, wherein the n electric field strength measurement devices are arranged so that the states of the electromagnetic fields which occur from the electromagnetic field generators changing due to existence of the object can be measured separately from one another.

5. The object state detection apparatus according to claim 1, wherein the at least one processor is configured to convert m×n electric field strength values at the time when the space is in a still state into vector data with m×n elements.

6. The object state detection apparatus according to claim 1, wherein the apparatus executes alarm processing in accordance with the state identification by the at least one processor.

7. The object state detection apparatus according to claim 1, wherein the apparatus performs processing of photographing data of the space in accordance with the state identification by the at least one processor.

8. A method for detecting a state of an object, the method comprising acts of:
    providing m (m>=1) transmitters near a space, the space being occupied by the object when the object is in a particular state;
    identifying and measuring electric field strength which occurs from each of the m transmitters by n (n>=1) receivers;
    calculating characteristics from time-series data of m×n electric field strength; and
    identifying, by statistical processing, the state of the object from the characteristics and characteristic data collected in each of a plurality of still states of the object, wherein an upper-limit value and a lower-limit value of the electric field strength is learned for each time-series data based on characteristic data of each still state which has been collected, and wherein the state is identified by the fact that input characteristic data is between the upper-limit value and the lower-limit value of the electric field strength or the state is identified by the fact that the input characteristic data is not between the upper-limit value and the lower-limit value of the electric field strength, the input characteristic data being time-series data comprising the amount of fluctuation of the time series data of the m×n electric field strength for a predetermined period.

9. The object state detection method according to claim 8, wherein each of the transmitters has an antenna structure for controlling spatial distribution of accumulated fields.

10. The object state detection method according to claim 8, wherein an efficiency of radiation of an electromagnetic field into free space by each of the transmitters changes when the object exists nearby.

11. The object state detection method according to claim 8, wherein the n receivers are arranged so that the states of electromagnetic fields which occur from the transmitters changing due to existence of the object can be measured separately from one another.

12. The object state detection method according to claim 8, wherein the act of calculating characteristics includes converting m×n electric field strength values at the time when the space is in a still state into vector data with m×n elements.

13. The object state detection method according to claim 8, wherein alarm processing is executed in accordance with identifying the state of the object.

14. The object state detection method according to claim 8, wherein processing of photographing data of the space is performed in accordance with identifying the state of the object.

* * * * *